(12) United States Patent
Evans et al.

(10) Patent No.: US 8,931,536 B2
(45) Date of Patent: Jan. 13, 2015

(54) DEVICES FOR APPLYING CONDUCTIVE GEL-PADS TO ELECTRODES AND ELECTRODES PRODUCED THEREBY

(75) Inventors: Thomas D. Evans, Opelika, AL (US); John Mann, Auburn, AL (US); Todd Evans, New Baltimore, MI (US); Terrence A. Precht, Loveland, CO (US); Eric M. Krug, Loveland, CO (US); Fred William Kreiner, Boulder, CO (US); Helmuth Otto Kroog, Loveland, CO (US)

(73) Assignee: Ropheka Technologies, LLC, Auburn, AL (US)

( * ) Notice: Subject to any disclaimer, the term of this patent is extended or adjusted under 35 U.S.C. 154(b) by 1803 days.

(21) Appl. No.: 12/176,706

(22) Filed: Jul. 21, 2008

(65) Prior Publication Data

US 2009/0155594 A1  Jun. 18, 2009

Related U.S. Application Data

(60) Provisional application No. 61/066,154, filed on Jul. 20, 2007.

(51) Int. Cl.
*B32B 9/04* (2006.01)
*A61B 5/0408* (2006.01)

(52) U.S. Cl.
CPC ....... *A61B 5/04087* (2013.01); *A61B 2562/125* (2013.01)
USPC .............................. 156/538; 156/446; 156/191

(58) Field of Classification Search
CPC .............. H01M 10/0409; B65H 18/10; B65H 2301/414326; B65H 2301/4148; B65H 39/16; A61B 2562/125; A61B 5/04087
USPC ........................................................ 156/538
See application file for complete search history.

(56) References Cited

U.S. PATENT DOCUMENTS

| | | | | |
|---|---|---|---|---|
| 3,584,182 A | | 6/1971 | Volk | |
| 4,094,244 A | * | 6/1978 | Edwards et al. | 101/66 |
| 4,458,696 A | | 7/1984 | Larimore | |
| 4,712,460 A | * | 12/1987 | Allen et al. | 83/208 |
| 4,826,102 A | * | 5/1989 | Kato et al. | 242/332.5 |
| 4,827,939 A | | 5/1989 | Cartmell et al. | |
| 5,059,275 A | * | 10/1991 | Fukuda | 156/511 |
| 5,372,125 A | | 12/1994 | Lyons | |
| 5,405,482 A | * | 4/1995 | Morrissette et al. | 156/364 |

(Continued)

OTHER PUBLICATIONS

PCT International Search Report dated Oct. 8, 2008 for International Application No. PCT/US08/70617.

*Primary Examiner* — Philip Tucker
*Assistant Examiner* — Vicki Wu
(74) *Attorney, Agent, or Firm* — Gardner Groff Greenwald & Villanueva, P.C.

(57) ABSTRACT

Described herein are devices for applying conductive gels to electrodes and the gel-laminated electrodes produced thereby. The devices permit the reuse of the electrodes by easily applying fresh gels to them for each subsequent use. In a first example embodiment, all of the components of the laminating device are provided in a single housing. In a second example embodiment, the gel applying and drive components are housed within the device, and a replaceable cartridge houses the gels and the gel delivery components. Also described herein are dispensers for storing and dispensing conductive gels that can be readily applied to and removed from an electrode.

20 Claims, 23 Drawing Sheets

(56) References Cited

U.S. PATENT DOCUMENTS

| | | |
|---|---|---|
| 5,843,155 A | 12/1998 | Axelgaard |
| 5,904,712 A | 5/1999 | Axelgaard |
| 6,038,485 A | 3/2000 | Axelgaard |
| 6,263,226 B1 | 7/2001 | Axelgaard et al. |
| 6,347,246 B1 | 2/2002 | Perrault et al. |
| 6,418,333 B1 | 7/2002 | Axelgaard |
| 6,547,229 B1 * | 4/2003 | Hanson et al. ............ 270/52.09 |
| 6,596,105 B2 * | 7/2003 | Kendall, Jr. .................... 156/64 |
| 6,600,957 B2 | 7/2003 | Gadsby |
| 6,643,532 B2 | 11/2003 | Axelgaard |
| 6,743,223 B1 * | 6/2004 | Lang .............................. 606/32 |
| 6,757,560 B1 | 6/2004 | Fischer et al. |
| 7,213,628 B2 | 5/2007 | Nagate et al. |
| 8,168,033 B1 * | 5/2012 | Mohamad Nor .............. 156/285 |
| 2001/0052220 A1 * | 12/2001 | Usui et al. .................... 53/381.1 |
| 2004/0077991 A1 | 4/2004 | Kumar et al. |
| 2004/0193089 A1 | 9/2004 | Fischer et al. |
| 2004/0226650 A1 * | 11/2004 | Galles et al. ................. 156/247 |

* cited by examiner

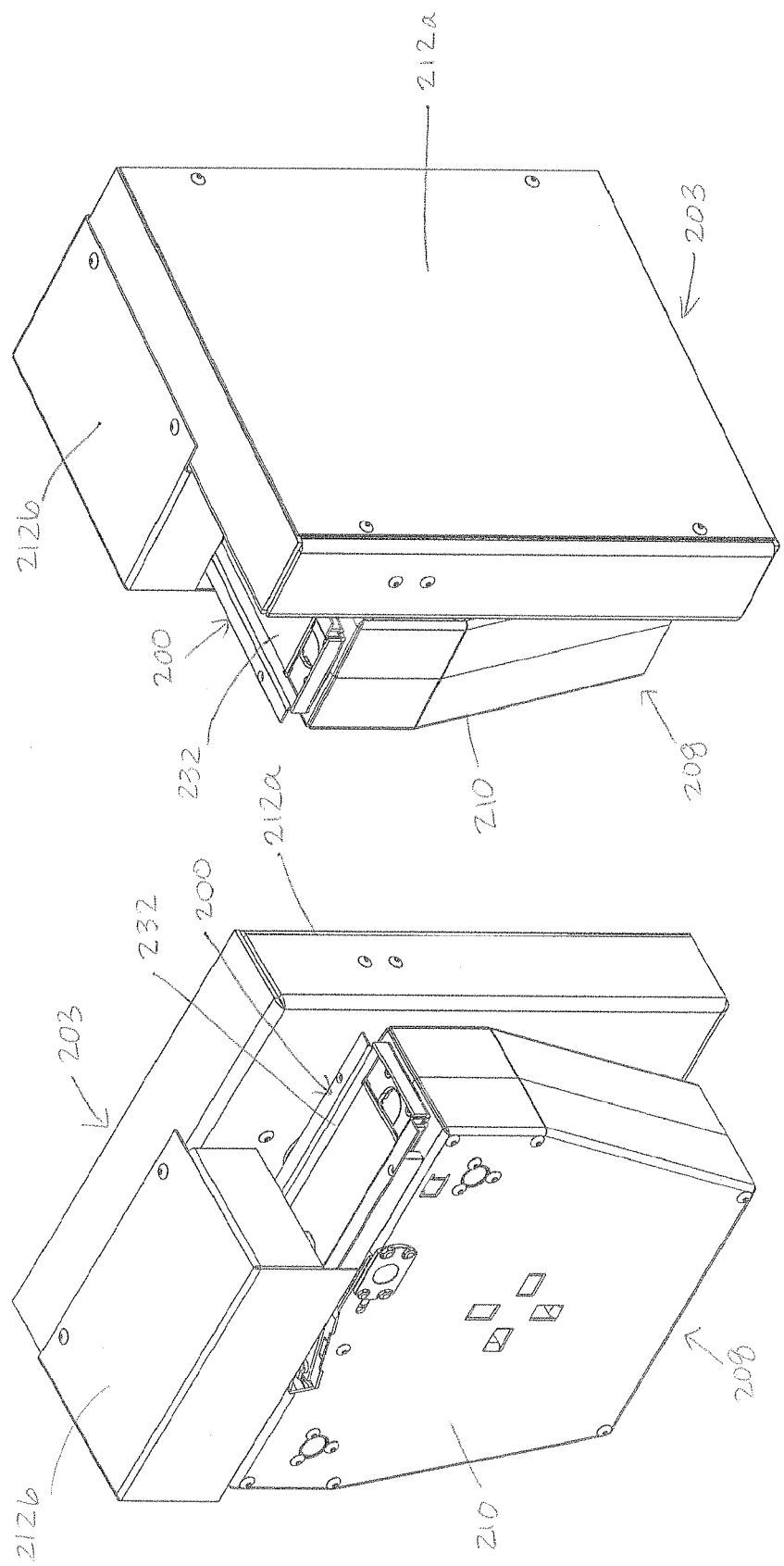

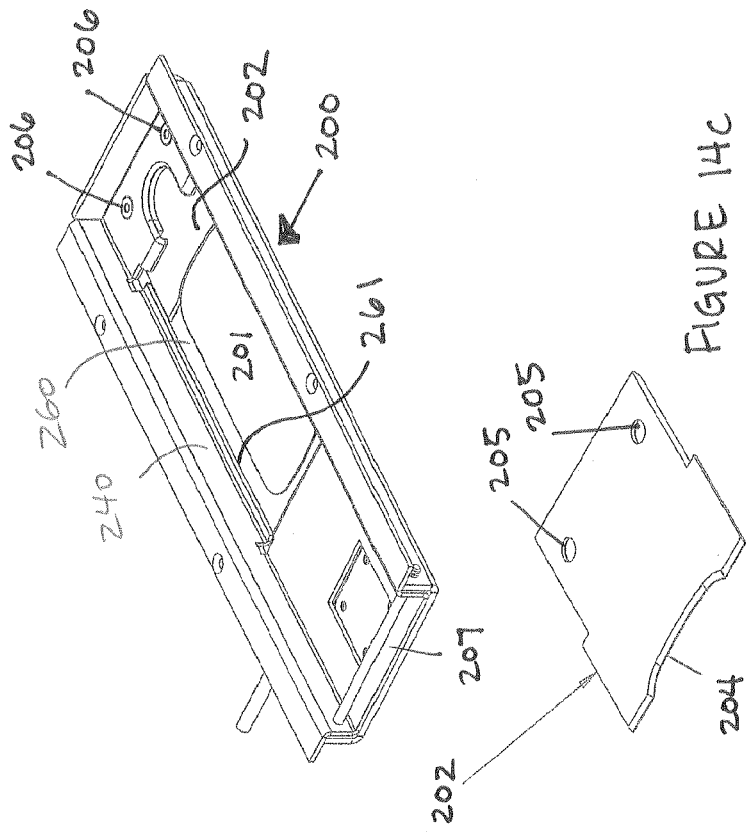
FIGURE 14b
FIGURE 14c
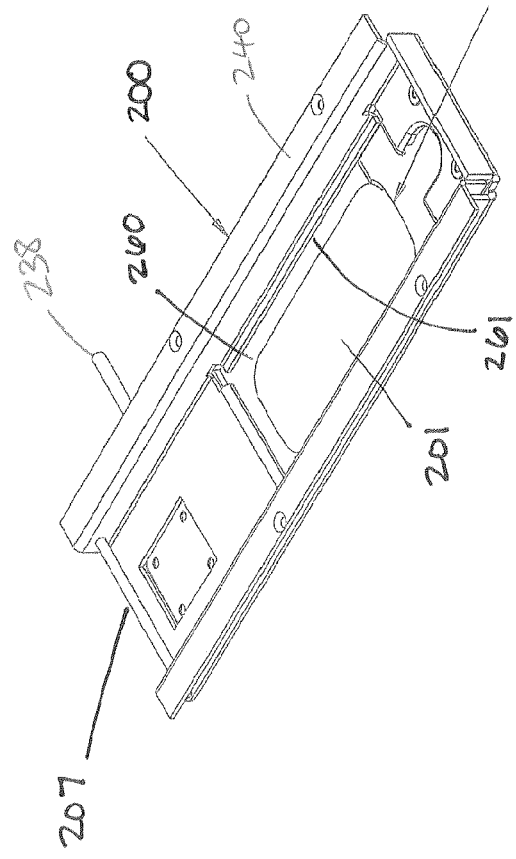
FIGURE 14a

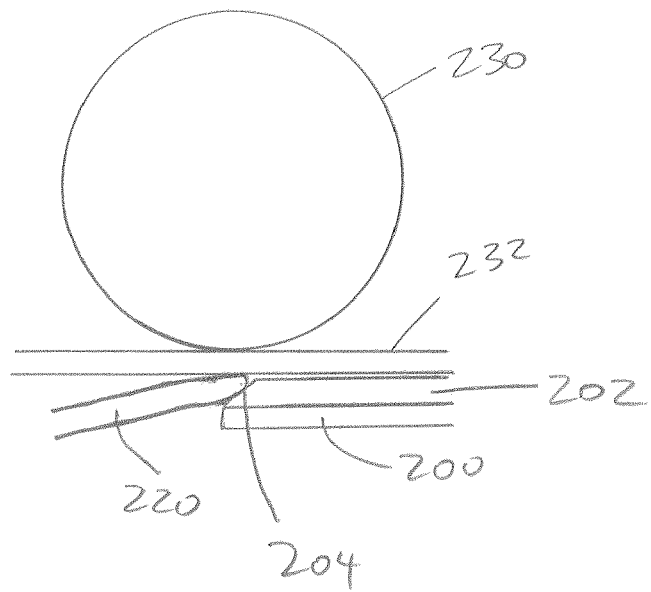

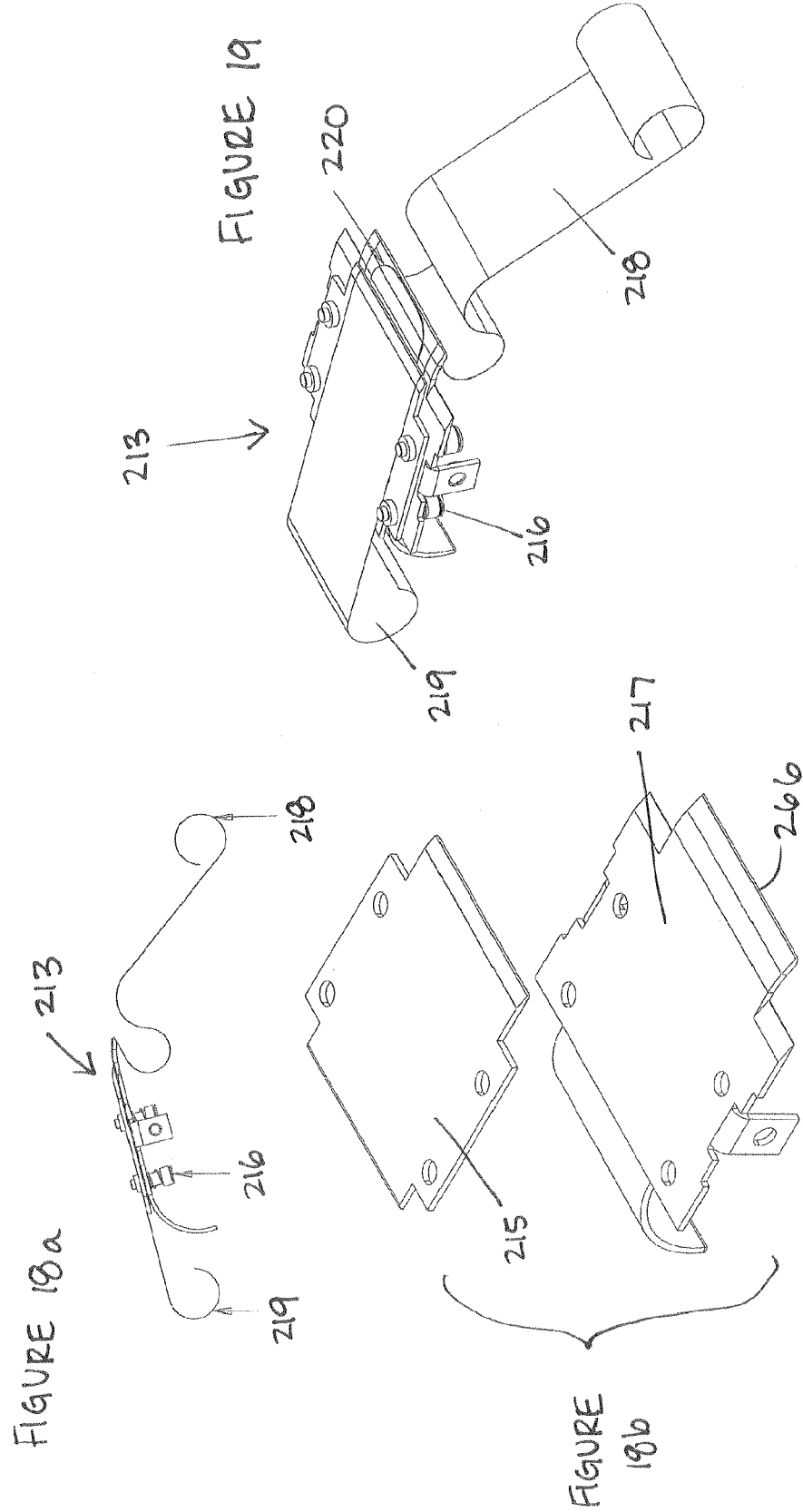

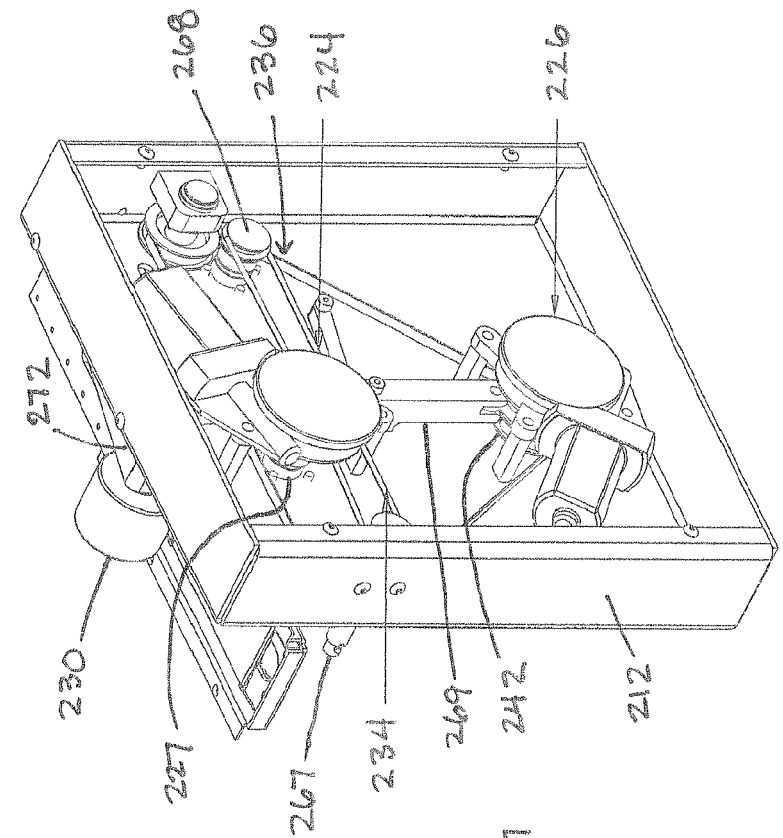
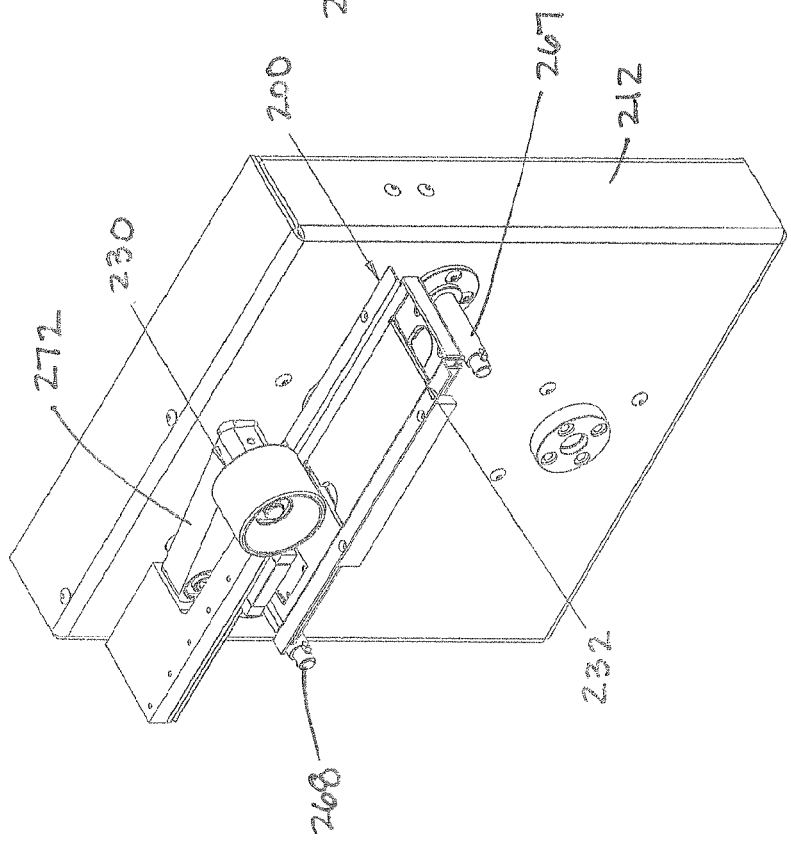

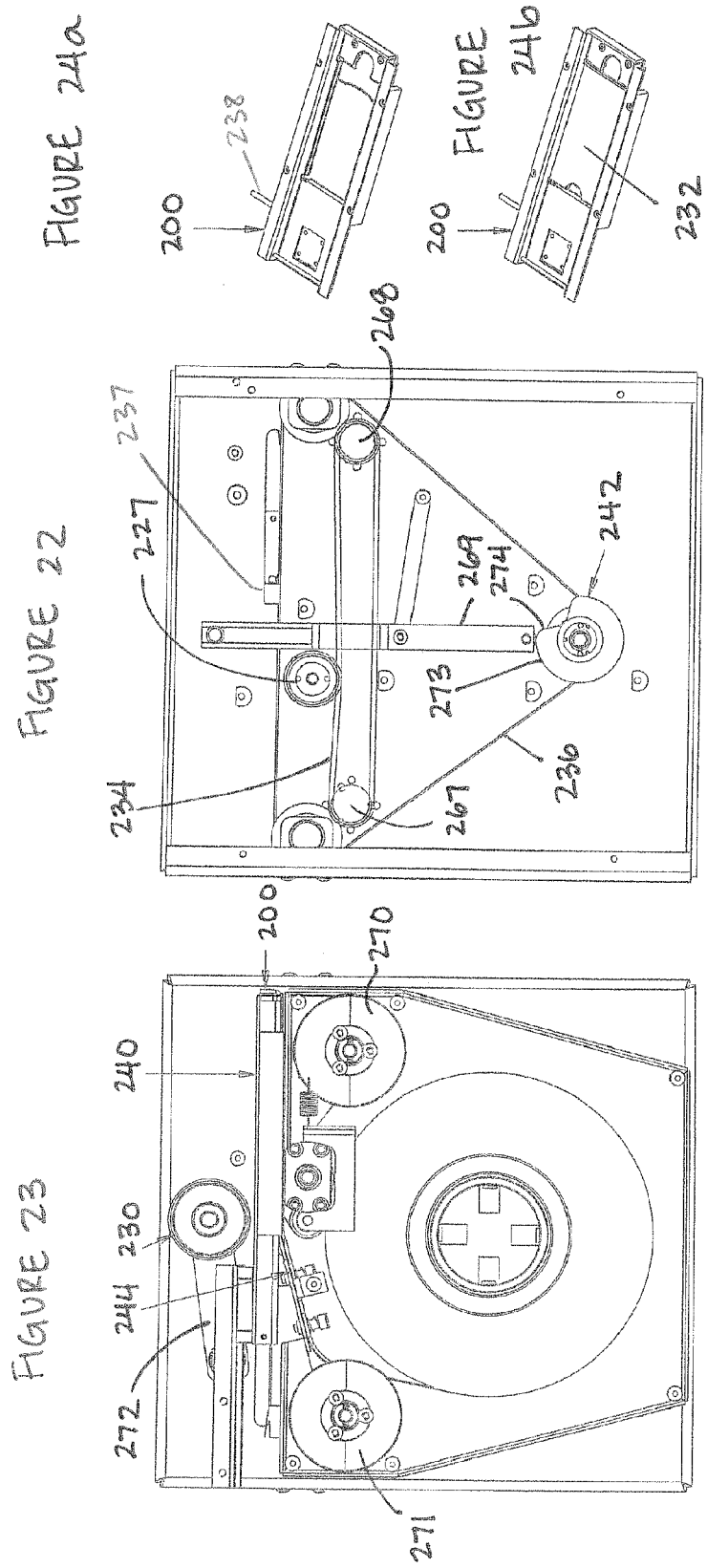

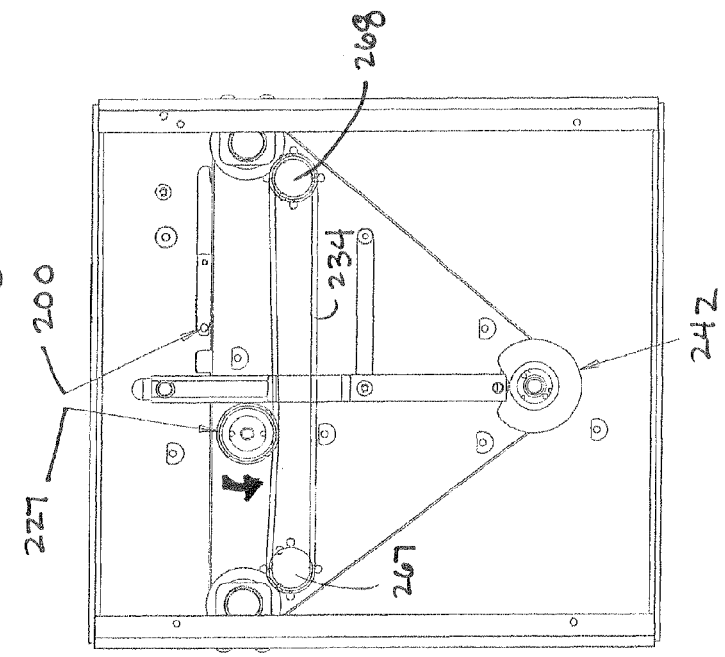
FIGURE 33
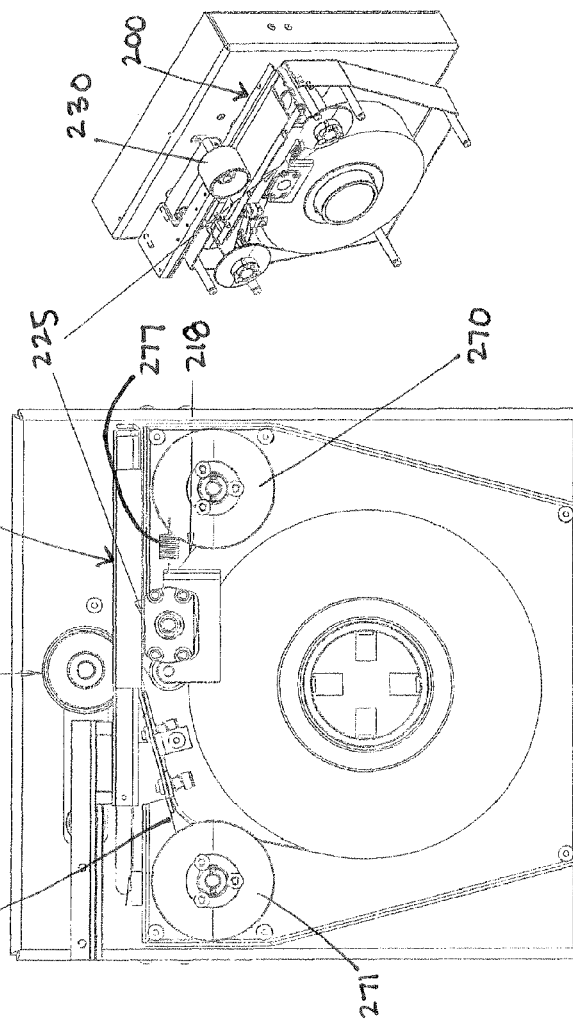
FIGURE 35
FIGURE 34

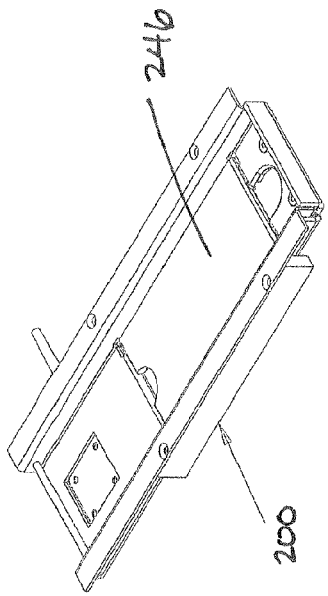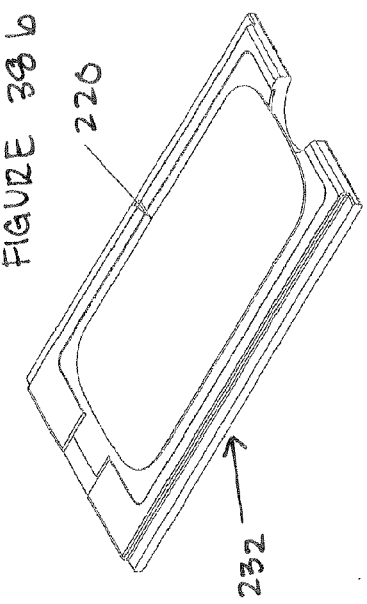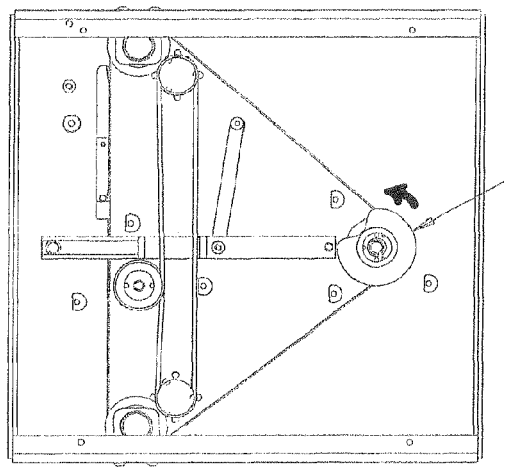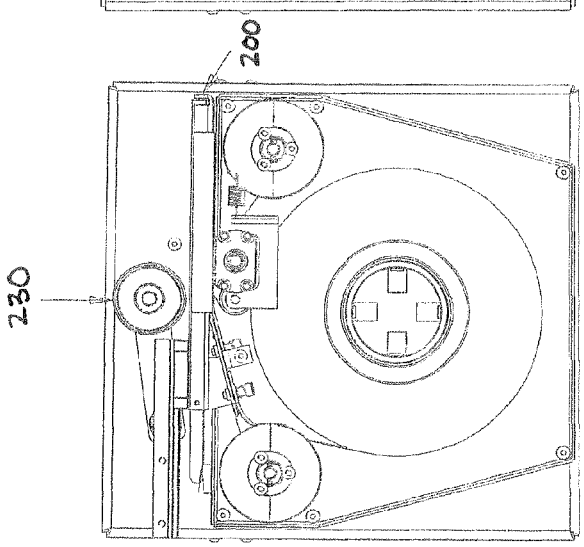

US 8,931,536 B2

DEVICES FOR APPLYING CONDUCTIVE GEL-PADS TO ELECTRODES AND ELECTRODES PRODUCED THEREBY

CROSS-REFERENCE TO RELATED APPLICATION

This application claims the priority benefit of U.S. Provisional Patent Application Ser. No. 61/066,154 filed Jul. 20, 2007, which was originally filed as a non-provisional patent application (U.S. Non-Provisional patent application Ser. No. 11/780,699 filed Jul. 20, 2007) and subsequently converted to a provisional patent application, the entire scope and content of which is hereby incorporated herein by reference.

TECHNICAL FIELD

The present invention relates generally to therapeutic devices for applying electric energy to the body and, in particular, to electrodes with conductive gel-pads and assembly devices therefor.

BACKGROUND OF THE INVENTION

Electrically conductive adhesive solid hydrogels and liquid gels are used in the medical field to provide an electrical interface to the skin of a subject to couple electrical signals into and/or out of the subject (e.g. for diagnostic and/or monitoring uses) and/or to couple electrical stimulus into the subject (e.g. for treatment and/or preventative uses). The application of these conductive materials to electrodes is known. In general, the conductive material is applied to the electrode using sophisticated equipment, where the equipment is located at the manufacturer. Moreover, the conductive material is applied to the electrode in a manner such that the material cannot be removed from the electrode and reused. Thus, these electrodes are intended to be disposable and not reused from patient to patient, making them costly and inefficient to use. This is due to the fact that once the electrode with conductive material has been in contact with a first patient, it is generally not desirable to apply the same electrode with the same conductive material to a different patient.

Accordingly, it can be seen that needs exist for improved electrodes that are reusable. In addition, there is a need for a device that can be used on-site to reapply fresh gel-pads to the electrodes for subsequent reuse. It is to the provision of solutions meeting these and other needs that the present invention is primarily directed.

SUMMARY OF THE INVENTION

Described herein are devices for applying conductive gels to electrodes and the gel-laminated electrodes produced thereby. The devices permit the reuse of the electrodes by easily applying fresh gels to them for each subsequent use. In a first example embodiment, all of the components of the laminating device are provided in a single housing. In a second example embodiment, the gel applying and drive components are housed within the device, and a replaceable cartridge houses the gels and the gel delivery components. Also described herein are dispensers for storing and dispensing conductive gels that can be readily applied to and removed from an electrode.

The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying figures, which are incorporated in and constitute a part of this specification, illustrate several aspects of the invention which are described below.

FIG. 12 is a left perspective view of a laminating device according to a second example embodiment of the present invention, showing the device in use with a replaceable gel-pad cartridge.

FIG. 13 is a right perspective view of the laminating device and gel-pad cartridge of FIG. 12.

FIG. 14A is a front/left perspective view of a carriage and a blade secured within the carriage of the laminating device of FIG. 12.

FIG. 14B is a rear/left perspective view of the carriage and blade assembly of FIG. 14A.

FIG. 14C is a rear/left perspective view of the blade of FIG. 14A.

FIG. 14D is a side detail view of the blade of FIG. 14A in use, showing the electrode and a leading edge of the blade compressing the leading edge of the gel-pad at a pinching zone.

FIG. 18A is a side view of a separator mechanism of the gel-pad cartridge assembly of FIG. 12 showing the gel-pad tape routed therethrough.

FIG. 18B is an exploded perspective view of separating plates of the separator mechanism of FIG. 18A.

FIG. 19 is a perspective view of the separator mechanism of FIG. 18A.

FIG. 20 is a front/left perspective view of the laminating device of FIG. 12 with the overhanging housing portion removed to show the interior components.

FIG. 21 is a front/right perspective view of the laminating device of FIG. 12 with a right sidewall removed to reveal the interior components.

FIG. 22 is a right side view of the laminating device of FIG. 12 with the right sidewall and drive motors removed to reveal the interior components in an idle/home position.

FIG. 23 is a left side view of the laminating device and the gel-pad cartridge of FIG. 12 with the respective left sidewalls removed to reveal the interior components in the idle/home position.

FIG. 24A is a perspective view of the carriage of FIG. 14A without an electrode.

FIG. 24B is a perspective view of the carriage of FIG. 14A with an electrode.

FIG. 33 is a right side view of the laminating device of FIG. 12 with the right sidewall and the drive motors removed to show the internal components in a done position.

FIG. 34 is a left side view of the laminating device of FIG. 12 with the left sidewall and the overhanging housing portion removed to show the internal components in the done position.

FIG. 35 is a front/left perspective view of the laminating device of FIG. 34.

FIG. 36 is a right side view of the laminating device of FIG. 12 with the right sidewall and the drive motors removed to show the internal components returned to the idle/home position of FIGS. 27-28.

FIG. 37 is a left side view of the laminating device of FIG. 12 with the left sidewall and the overhanging housing portion removed to show the internal components returned to the idle/home position of FIGS. 27-28.

FIG. 38A is a top perspective view of the carriage of FIG. 14A carrying an electrode laminated with a gel-pad.

FIG. 38B is a bottom perspective view of the electrode of FIG. 38 showing the gel-pad applied thereto.

DETAILED DESCRIPTION OF EXAMPLE EMBODIMENTS OF THE INVENTION

Figure 1:
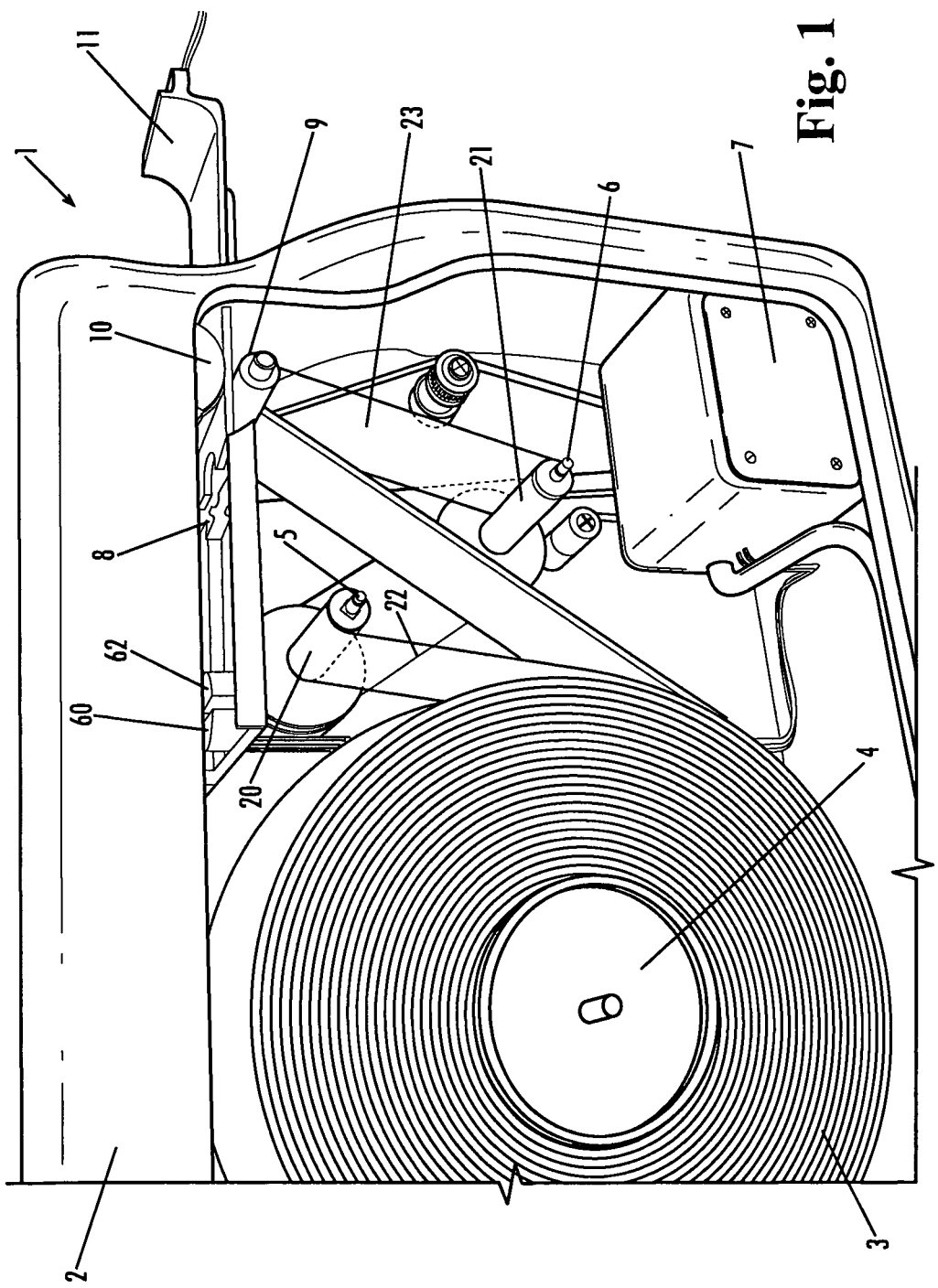
FIG. 1 is a side perspective view of a portion of a laminating device according to a first example embodiment of the present invention, with a side access door removed to show the internal components of the device.

The materials, articles, devices, and/or methods described herein may be understood more readily by reference to the following detailed description of example embodiments and the appended figures. It is to be understood that the invention is not limited to the specific devices, methods, conditions, or parameters described and/or shown herein, and that the terminology used herein is for the purpose of describing particular embodiments by way of example only. Thus, the terminology is intended to be broadly construed and is not intended to be unnecessarily limiting of the claimed invention. For example, as used in the specification including the appended claims, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Throughout the description and claims of this specification, the word "comprise" and other forms of the word, such as "comprising" and "comprises," means including but not limited to, and is not intended to exclude, for example, other additives, components, or steps.

The term "electrode" as used herein is any conductive element that can apply an electrical current to a subject. The conductive element (in its assembled state) includes a base, a conductive gel applied thereto, and lead wire connected to the conductive gel to maintain constant current.

The term "conductive gel" as used herein is any polymeric material that when applied to the surface of the electrode permits the flow of electric current from the electrode through the material to the subject when in contact with the subject. Examples of conductive gels useful herein are provided below. The conductive gel is also referred to herein as the "gel-pad."

The term "removable" in reference to the conductive gel is the ability of the conductive gel to be easily removed from the surface of the electrode without any special tools. For example, the conductive gel is "removable" if it can be easily peeled off of the electrode.

Described herein are laminating devices for applying removable conductive gel-pads to the bases of electrodes. The laminating devices each include at least one housing defining an opening for receiving the electrodes, an applicator mechanism in the housing that is adapted to apply the conductive gel-pads to the bases of the electrodes, a delivery mechanism in the housing that is adapted to deliver the conductive gel-pads to the applicator mechanism, and a drive mechanism in the housing that is adapted to drive the gel-pad delivery mechanism and the gel-pad applicator mechanism.

FIGS. 1, 3, 4, and 7 show a laminating device 1 according to a first example embodiment of the present invention. FIG. 1 shows the internal features of the laminating device 1. The laminating device 1 includes a housing 2 that is generally composed of a durable, lightweight material such as plastic. As will be discussed below, the laminating devices described herein can be portable. Thus, the selection of housing materials can vary depending upon the intended end-use of the device.

Figure 5:
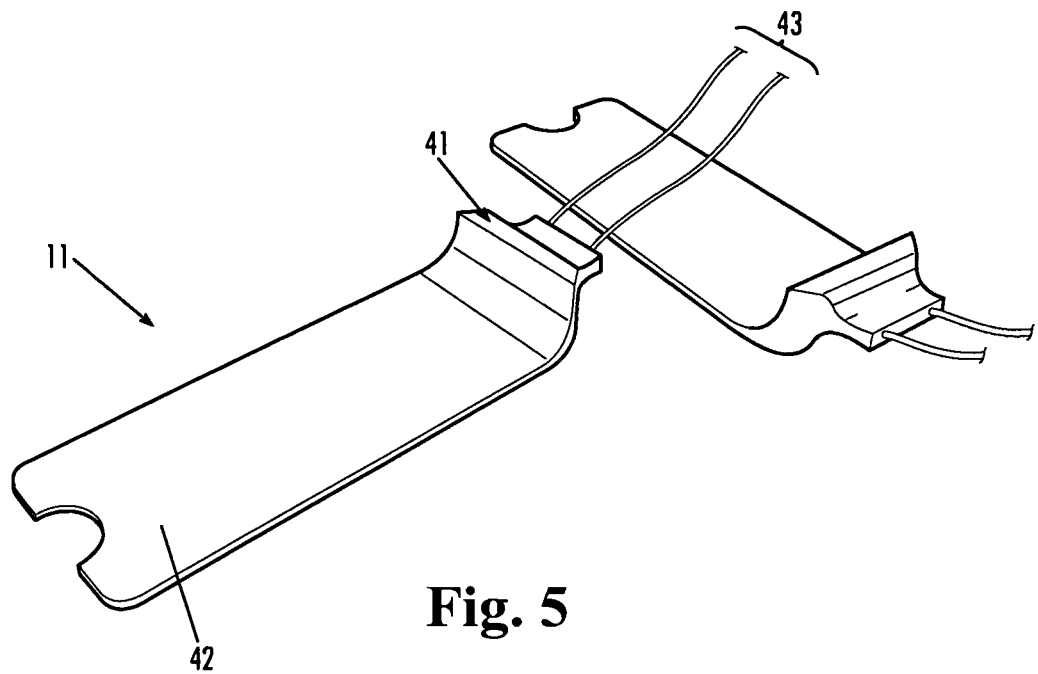
FIG. 5 is a perspective view of an electrode laminated by the laminating device of FIG. 1.
Figure 6:
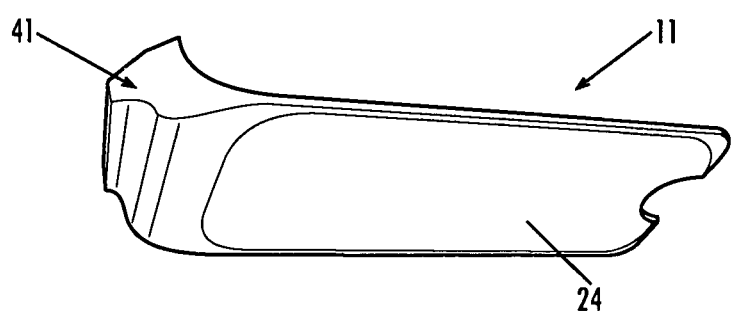
FIG. 6 is a bottom perspective view of the electrode of FIG. 5 showing the gel-pad laminated onto the bottom surface of the electrode.

Before further describing the details of this embodiment, some additional background will be useful. FIGS. 5 and 6 show an electrode 11 of a conventional design that is used in conjunction with the laminating device 1. The electrode 11 has a handle 41 extending from a base 42. The handle 41 and the base 42 can be made of the same or different material, for example, a durable, lightweight material such as plastic or rubber. The handle 41 and the base 42 can be a single molded article, as depicted, with both parts made of a conductive material. In other embodiments, the electrode is composed of a conductive material secured to a flexible backing. Lead wires 43 extend from the handle 41 so that the wires are in electrical contact with the conductive gel-pad 44 attached to the base 42 of the electrode 11. A variety of different electrode 11 designs and shapes can be laminated with the laminating devices described herein. The dimensions of the electrode can vary based upon the end-use or application of the electrode. As such, the present invention is not limited to use with the specific electrode design shown in FIGS. 5 and 6.

Figure 2:
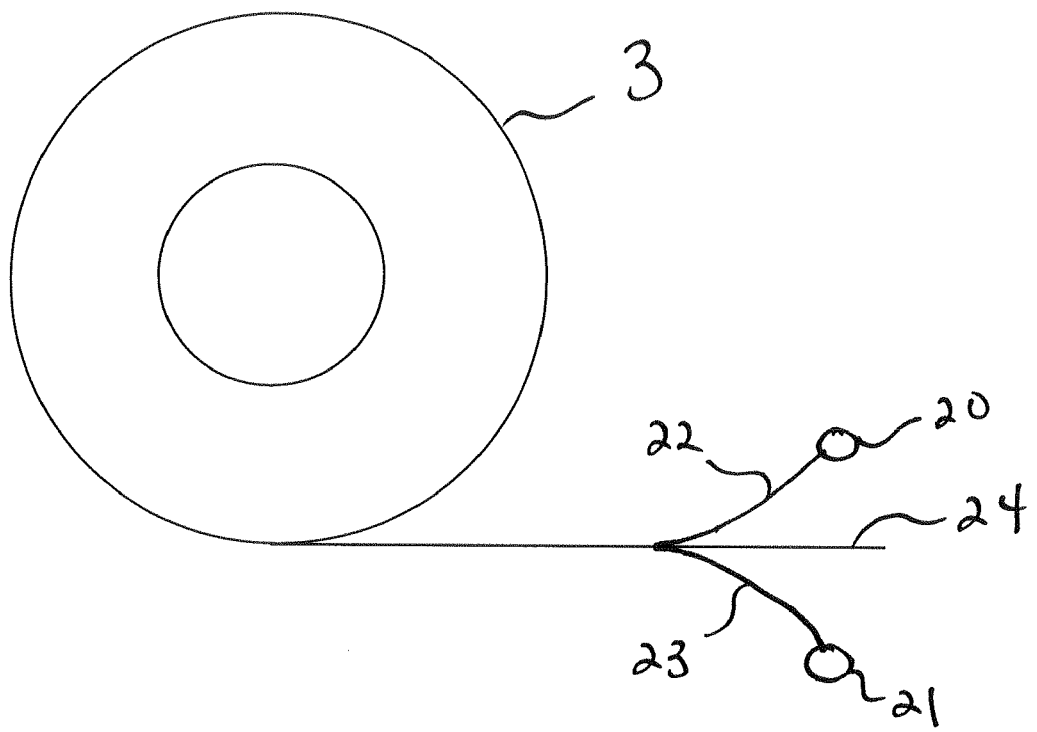
FIG. 2 is a side view of a roll of conductive gel-pads of the device of FIG. 1.
Figure 3:
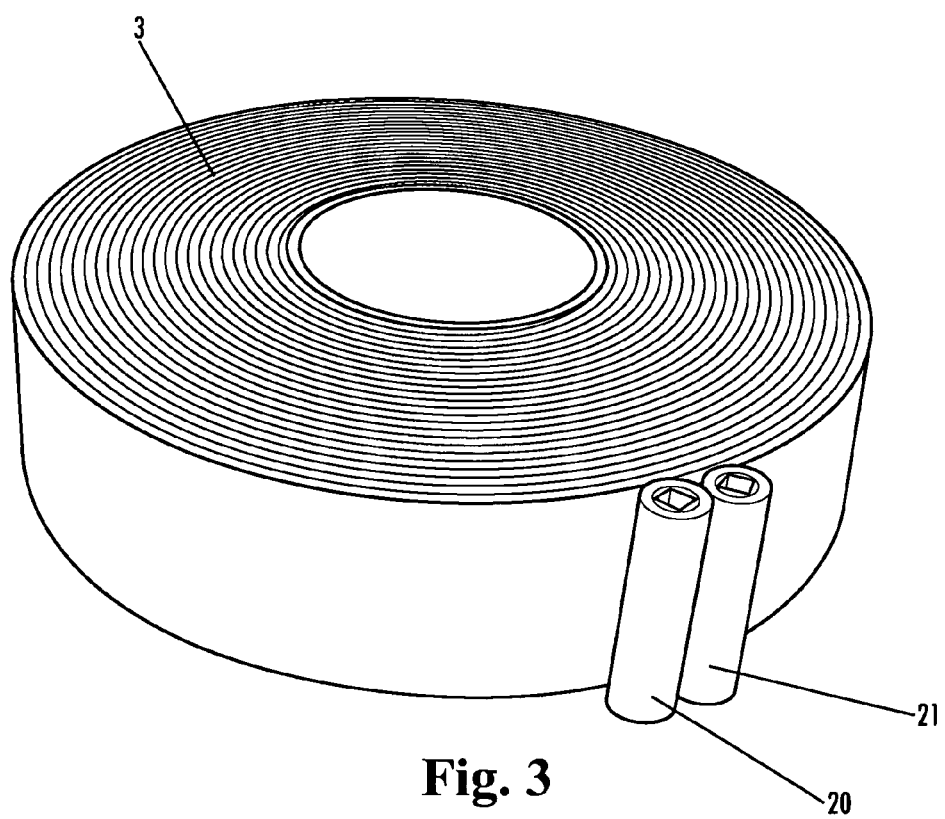
FIG. 3 is a perspective view of the roll of conductive gel-pads of FIG. 2.
Figure 8:
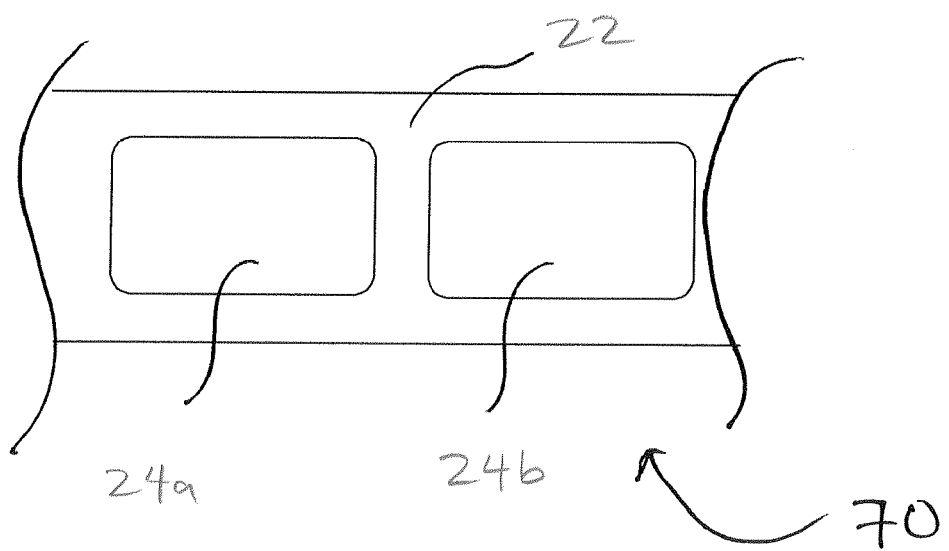
FIG. 8 is a top view of a portion of the conductive gel-pad tape of FIG. 2 showing two individual conductive gel-pads.

FIGS. 2, 3, and 8 show details of the conductive gel-pads 24a, 24b, etc. (collectively referred to herein as the "gel-pads 24"). Typically, a number of the gel-pads 24 are provided in a roll 3, with the gel-pads interposed between first and second protective liners 22 and 23 to form a tape. The shape of the gel-pads 24 is selected based on the shape of the electrodes 11. In the embodiment depicted in FIG. 8, the gel-pads 24 are separate pieces that are at least slightly spaced apart from each other. In the embodiment of FIGS. 2 and 3, the roll 3 includes a strip of the conductive gel that is preformed (e.g., by scoring or perforations) into separate gel-pads that contact each other. And in yet other embodiments, the roll 3 includes a continuous strip of the conductive gel and the laminating device includes a cutting mechanism that separates a length of the gel strip (i.e., one gel-pad) from the remainder of the gel strip when or after delivering the gel to the electrode.

The protective liners 22 and 23 can be any durable material that is strong enough to be readily peeled from the gel-pads 24. For example, the protective liners 22 and 23 can be made of a polymer such as, for example, polyethylene or a polyester (e.g., polyethylene terephthalate). In a typical commercial embodiment, the protective liners 22 and 23 are made of MYLAR.

The gel-pads 24 have an adhesive on each side for adhering to the protective liners 22 and 23. Once the protective liners 22 and 23 are removed, the adhesive is used to secure the gel-pads 24 to the electrodes 11 and to subjects. Preferably, the adhesive is conductive and biocompatible.

Any conductive gels commonly used in the art can be used herein. For example, the cationic polymers disclosed in U.S. Pat. No. 6,347,246 can be used herein. In other aspects, the polymers disclosed in U.S. Pat. Nos. 5,868,136; 6,038,464; and 6,115,625 can be used herein. In one aspect, the hydrogels produced by AmGel Technologies (e.g., AG602, AG603, AG702, AG703, AG704, AG803, and AG902) can be used herein. The selection of the conductive gel will vary depending upon, among other things, the materials used to produce the electrode and the intended end-use of the electrode.

Attached to the leading ends of the protective liners 22 and 23 are first and second connectors such as take-up clips 20 and 21. The take-up clips 20 and 21 are designed so that they are engaged by corresponding elements of the delivery mechanism of the laminating device 1, as described below.

Referring back to FIG. 1, the gel-pad delivery mechanism of the laminating device 1 includes a laminate spool 4 within the housing 2 for removably mounting the roll 3 of gel-pads 24. In this embodiment, the laminate spool 4 is designed such that the roll 3 of conductive gels 24 fits snuggly on the spool.

In addition, the delivery mechanism includes first and second take-up rollers 5 and 6, a first pressure roller 9, and at least one actuator 7. The first and second take-up clips 20 and 21 at the leading ends of the protective liners 22 and 23 can be removably secured to the respective first and second take-up rollers 5 and 6. For example, in the depicted embodiment the clips 20 and 21 are cylindrical and can be easily slipped over and secured to the take-up rollers 5 and 6. As depicted, take-up clip 20 slips over and secures to take-up roller 5 and take-up clip 21 slips over and secures to take-up roller 6. The clips 20 and 21 are secured to the rollers 5 and 6 by a snug fit, keyed features (e.g., a tab on the roller fits into a slot in the clip), conforming non-circular geometry (octagonal outer roller surface and octagonal inner clip surface), etc. The clips 20 and 21 are thus easily removed from the respective take-up rollers 5 and 6 once the conductive gel roll 3 is spent and needs to be replaced. In other embodiments, the leading ends of the protective liners are directly attached to the take-up rollers without the use of the clips.

The first and second take-up rollers 5 and 6 work to reel in the first and second liners 23, and as such the rollers may be in the form of conventional reels. The first take-up roller 5 rotates to reel in the first liner 22 and peel it away from the gel-pads 24 and the second liner 23 immediately upon unreeling from the roll 3. The second take-up roller 6 rotates to reel in the second liner 23 and to first pull it over and around the first pressure roller 9. The second liner 23 is pulled around the first pressure roller 9 at a sharp turn, thereby advancing the gel-pads 24 forward into a ready position (adjacent where the electrodes 11 will be positioned) while the second liner 23 is peeled back and reeled in.

The actuator 7 drives the first and second take-up rollers 5 and 6 and the first pressure roller 9. In particular, the rollers 5, 6, and 9 are driven by a linkage such as a belt or chain that is driven by the actuator 7. In other embodiments, the rollers 5, 6, and 9 are driven directly by dedicated actuators that operate in a coordinated fashion. The actuator 7 can be an electric motor or another conventional actuator adapted to drive the take-up rollers 5 and 6 and the pressure roller 9. The motor can be powered by conventional sources such as electrical outlets (e.g., 110 V), batteries, or a combination thereof. The motors can also provide power to other components of the laminating device 1, if necessary. Although FIG. 1 depicts the device 1 with the motor, in other embodiments the device can additionally or alternatively be operated manually. For example, the device can be provided with a hand-crank operably coupled to the rollers for manually delivering the conductive gel to the electrode.

Details of the applicator mechanism are shown in FIG. 1. A receiving tray 8 is aligned with the opening in the housing 2 for sequentially receiving the electrodes 11. The tray 8 can be of most any shape and size, and the dimensions will vary based upon the dimensions of the electrodes 11. The tray 8 serves as a support for the electrodes 11. The tray 8 also aligns the electrodes 11 with the conductive gel-pads 24 so that the conductive gel is applied evenly and consistently across the surface of the electrode. The tray 8 includes an access opening through which one of the gel-pads 24 can be applied to the electrode 11 supported on the tray. Finally, as will be discussed below, activation mechanisms present on the receiving tray 8 can advise the user to turn on the motor of the device 1.

Figure 1A:
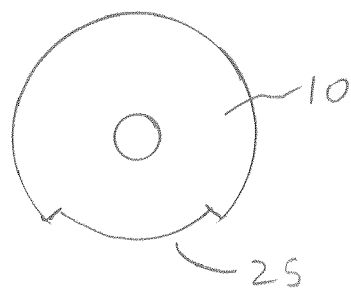
FIG. 1A is a side view of a second pressure roller of the device of FIG. 1 that cooperatively compresses gel-pads onto electrodes.

In addition, the applicator mechanism includes a second pressure roller 10 that cooperates with the first pressure roller 9 to apply a compression force to one of the gel-pads 24 (the one advanced to a ready position and separated from the liners 22 and 23) and one of the electrodes 11 (the one currently inserted into the tray 8). The pressure rollers 9 and 10 in general facilitate the formation of a good adhesive bond between the electrode 11 and the conductive gel 24. The second pressure roller 10 is also driven by the actuator 7, for example, by a linkage or by being directly coupled to the actuator. The second pressure roller 10 defines a recess 25 that receives the electrode 11 without compressing it against the gel-pad 24 when the roller 10 is in the ready position shown in FIG. 1A. In this way, an electrode 11 can be placed onto the tray 8 and easily pushed into the device 1 through the housing opening, with the electrode 11 sliding through the recess 25 to a ready position.

Figure 4:
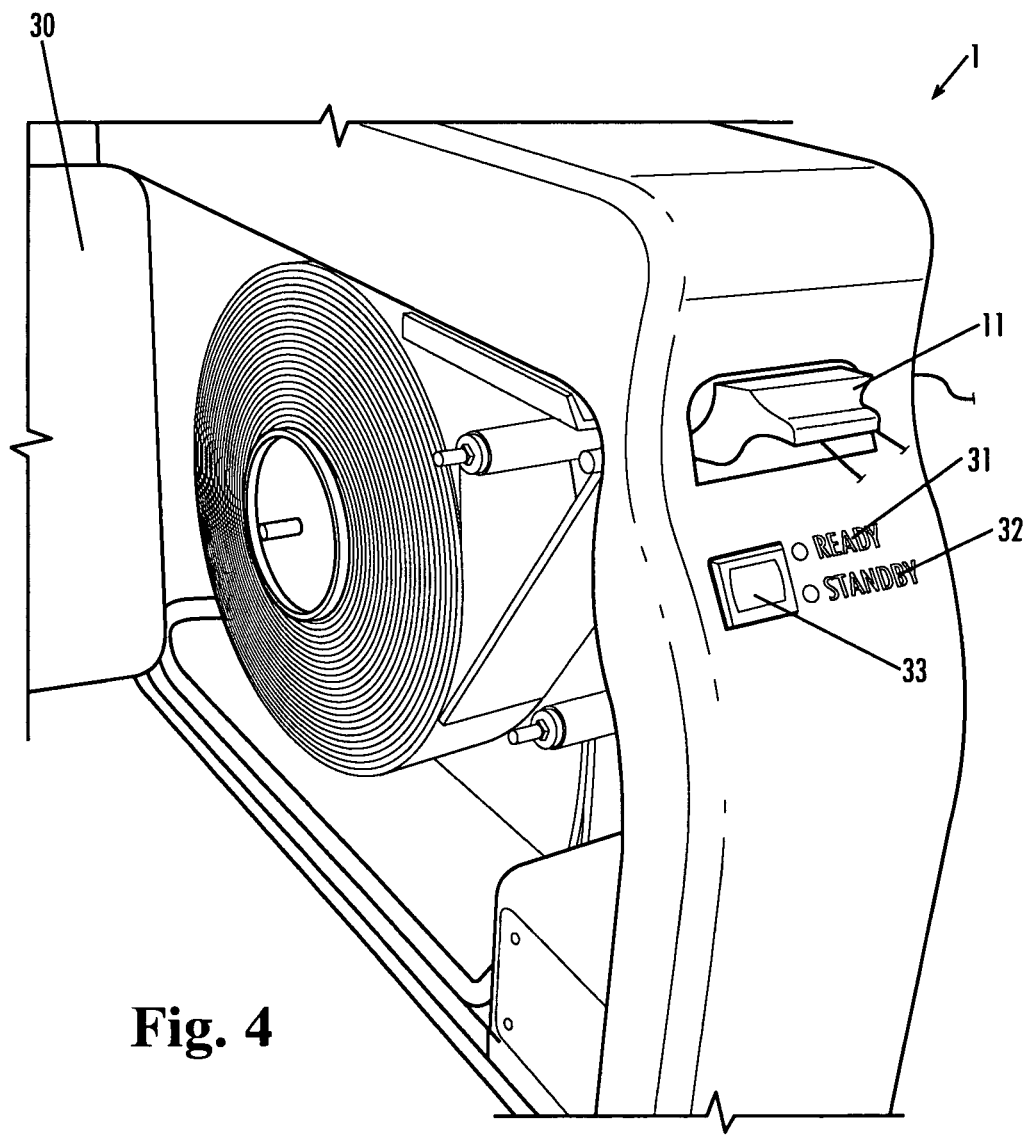
FIG. 4 a front/side perspective view of the device of FIG. 1 with the side access door opened.

Having described the major components of the laminating device 1, the use of the device for applying the conductive gel 24 to the electrode 11 now will be presented. As an initial matter, a roll 3 of conductive gel 24 is inserted into the device 1. Referring to FIG. 4, a side access door 30 of the housing 2 is opened, and a roll 3 of conductive gel 24 is placed on the spool 4. Take-up clip 20 is secured to take-up roller 5 and take-up clip 21 is secured to take-up roller 6 as described above. The conductive gel 24 is fed over pressure roller 9 so that there is no slack in the conductive gel tape, and the device is ready for use.

Figure 7:
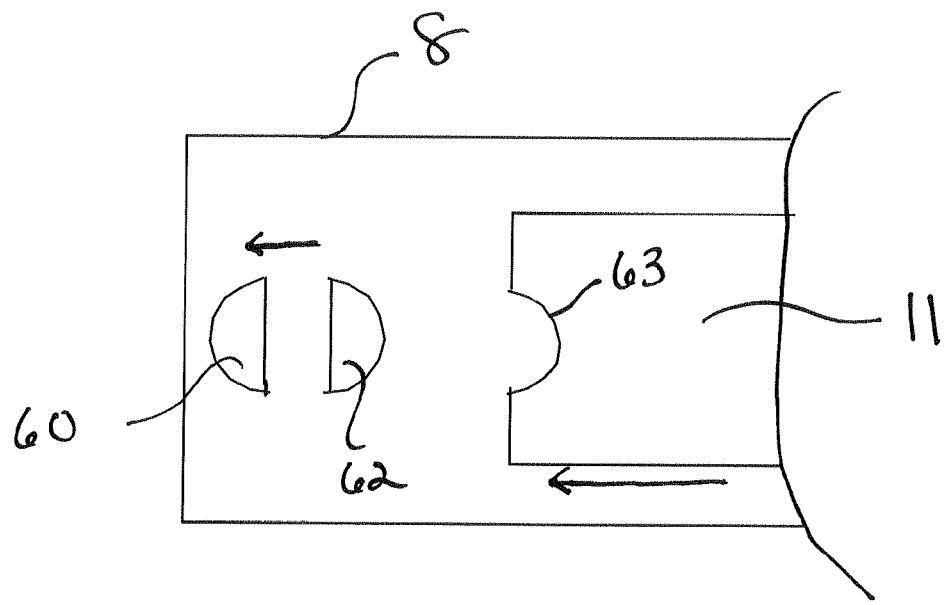
FIG. 7 is a top view of a receiving tray and activating mechanism of the device of FIG. 1.

Then one of the electrodes 11 is inserted into the housing opening of the laminating device 1 and onto the tray 8. The electrode 11 is inserted such that the side to be laminated faces downward. The electrode 11 is fully inserted until it engages an activation mechanism on the receiving tray 8. Referring to FIGS. 1 and 7, upon insertion of the electrode 11, the leading end (or another protruding portion) of the electrode (e.g., modified with a semi-circle indentation 63) engages an activation member 62 of the applicator mechanism. It is noted that the indentation and activation member can have other shapes than a semi-circle. The electrode 11 engages an activation member 62 and pushes it toward activation member 61. In other embodiments, a limit switch or other control device can be used for this function. When activation members 60 and 62 are in contact with one another, the electrode 11 cannot be inserted any further. Additionally, the device 1 will now indicate to the user that the device is ready for activation to begin the lamination process. As shown in FIG. 4, for example, when the electrode 11 is fully inserted into the device and the device is ready for activation, a ready light 31 will illuminate. If the activation mechanism has not been activated, the device will be in the stand-by position, and a stand-by light 32 will remain illuminated.

When the device is in the ready position, the motor is activated by the user pushing the start button 33. The motor rotates the take-up rollers 5 and 6 and the pressure rollers 9 and 10, with the pressure rollers rotating in opposite directions. With the rotation of the take-up rollers 5 and 6 and the pressure rollers 9 and 10, the conductive gel 24 is compressed onto the electrode 11 as the electrode is ejected from the dispenser. In other words, the pressure rollers 9 and 10 rotate with the electrode 11 and the gel-pad 24 compressed between them to force the gel-pad 24 to adhere to the electrode 11 and to force the laminated gel-pad out of the housing 2. This ensures the gel 24 is firmly attached to the electrode 11 by the time the electrode is ejected from the device 1.

In another aspect of the invention, there is provided a dispenser for dispensing a conductive gel. The dispenser includes a housing with a first opening for receiving a plurality of stacked conductive gels in the housing and a second opening for ejecting/dispensing the conductive gel, a spring mechanism that biases the gels toward the second opening, and a dispensing mechanism for dispensing the conductive gel.

Figure 9:
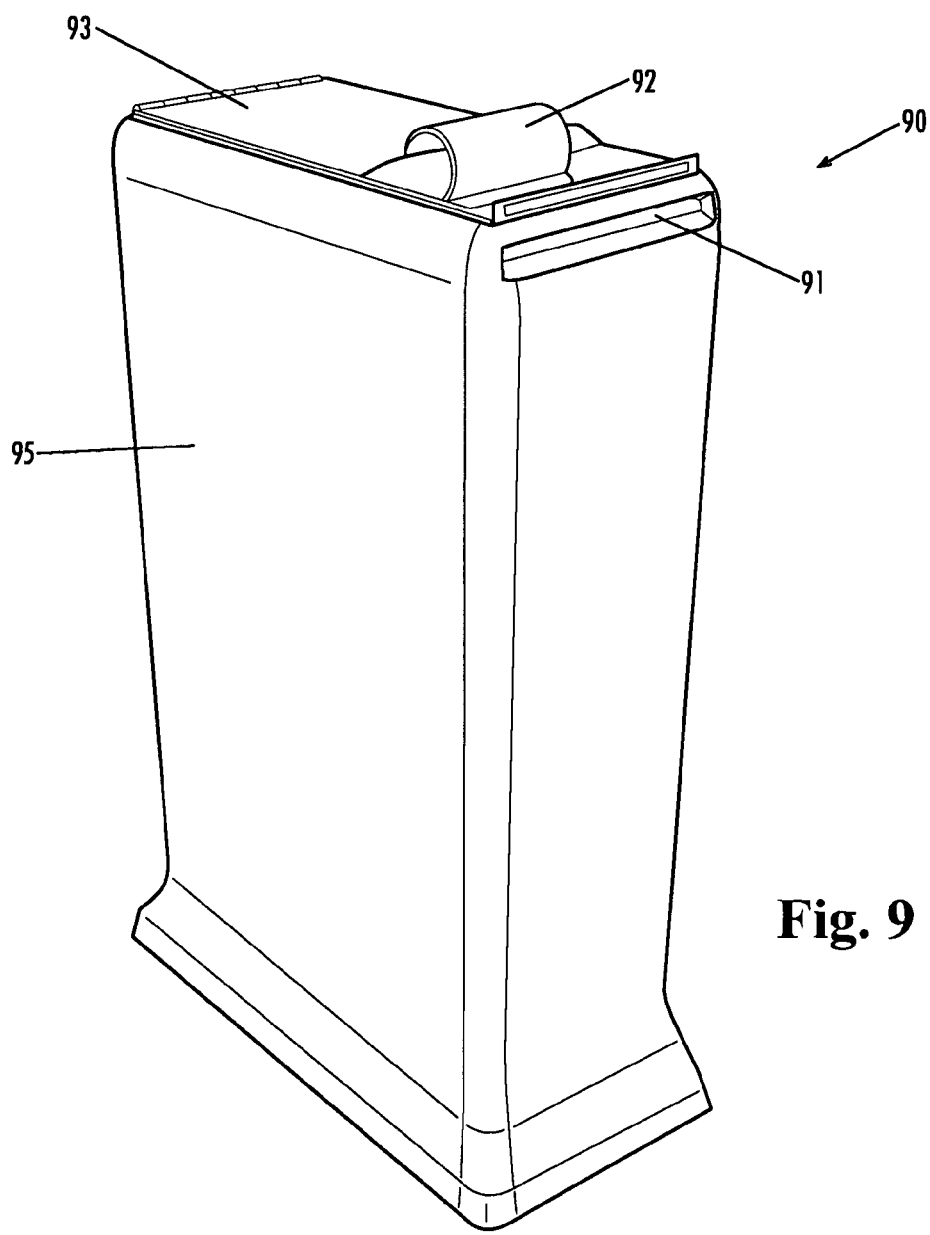
FIG. 9 is a perspective view of a conductive gel-pad dispenser according to another aspect of the present invention.
Figure 10:
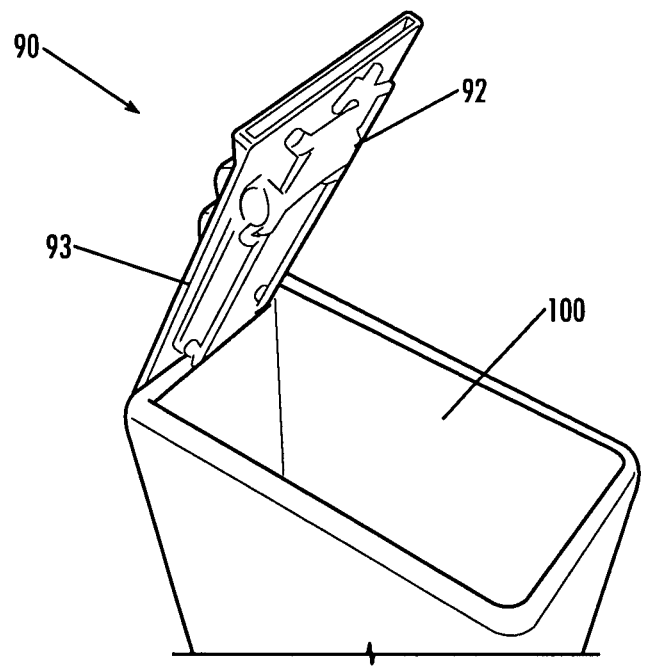
FIG. 10 is a top perspective view of a portion of the conductive gel dispenser of FIG. 9 with the top door open.
Figure 11:
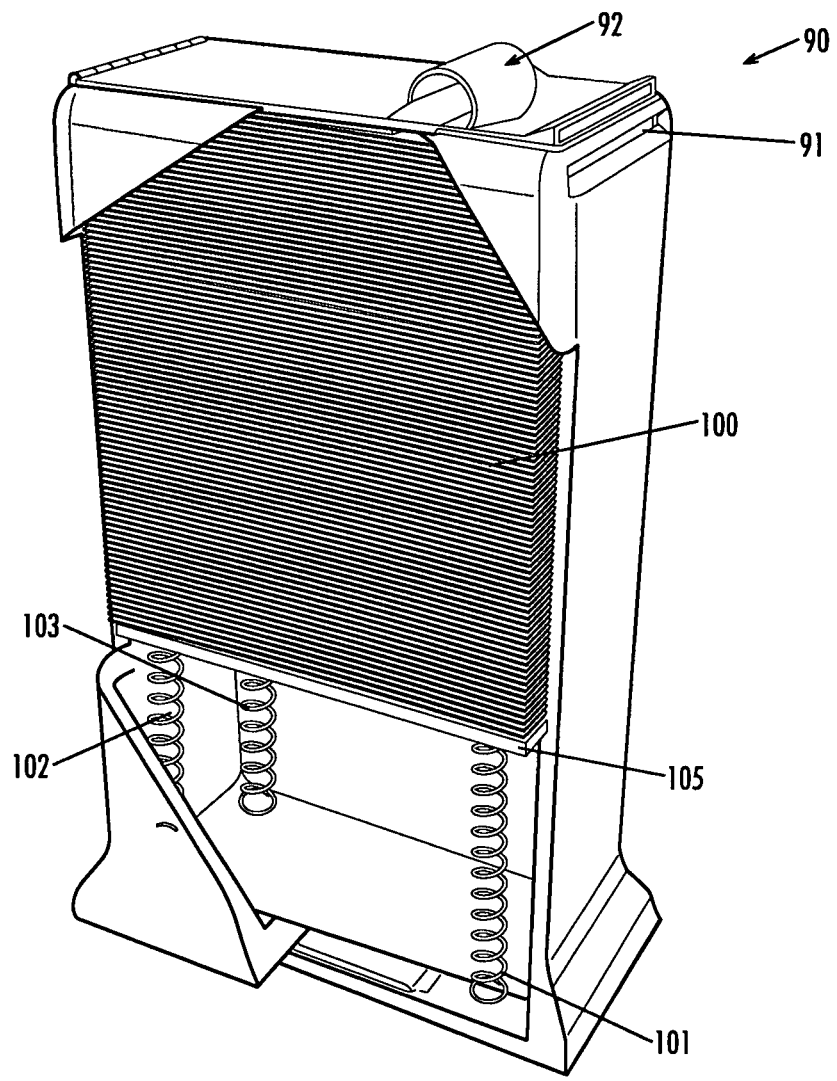
FIG. 11 is a top perspective view of a portion of the conductive gel dispenser of FIG. 9 with a portion of the sidewall removed to show the internal components.
Figure 14F:
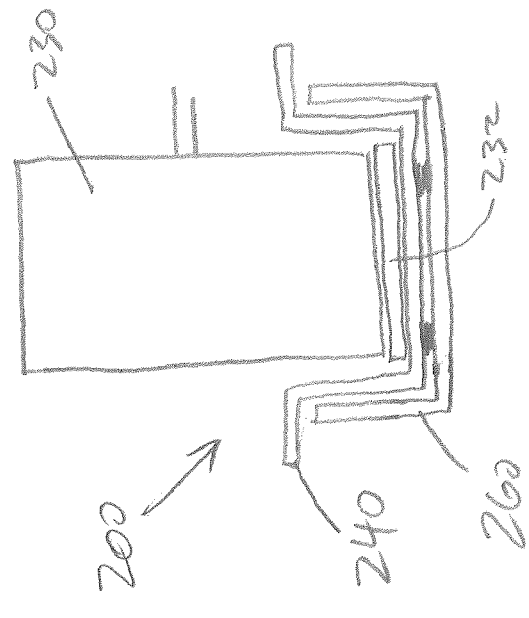
FIG. 14F is a detail front view of a portion of the laminating device of FIG. 14E showing the elevator in the raised position.
Figure 14E:
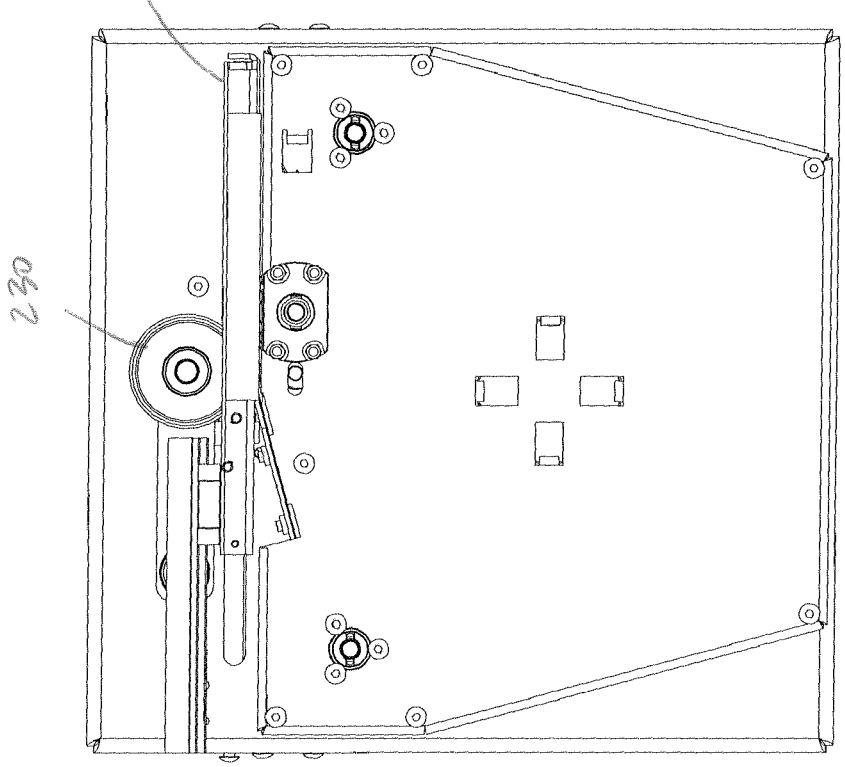
FIG. 14E is a right side view of the laminating device of FIG. 12 with the right sidewall removed to show the elevator in the raised position.
Figure 14H:
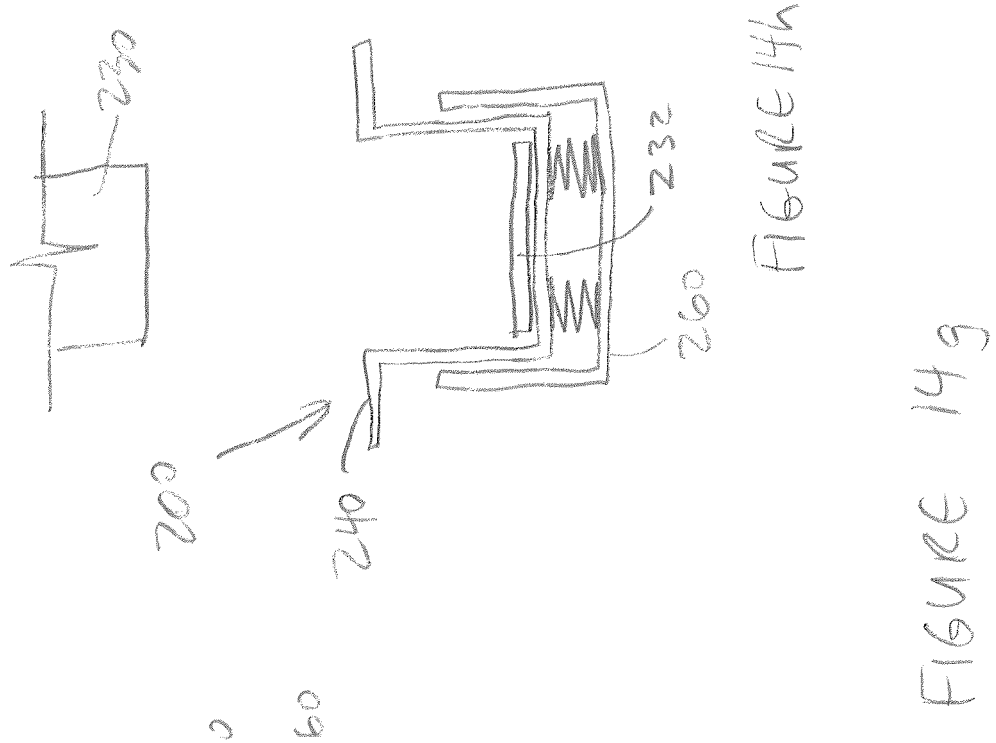
FIG. 14H is a detail front view of a portion of the laminating device of FIG. 14G showing the elevator in the lowered position.
Figure 14G:
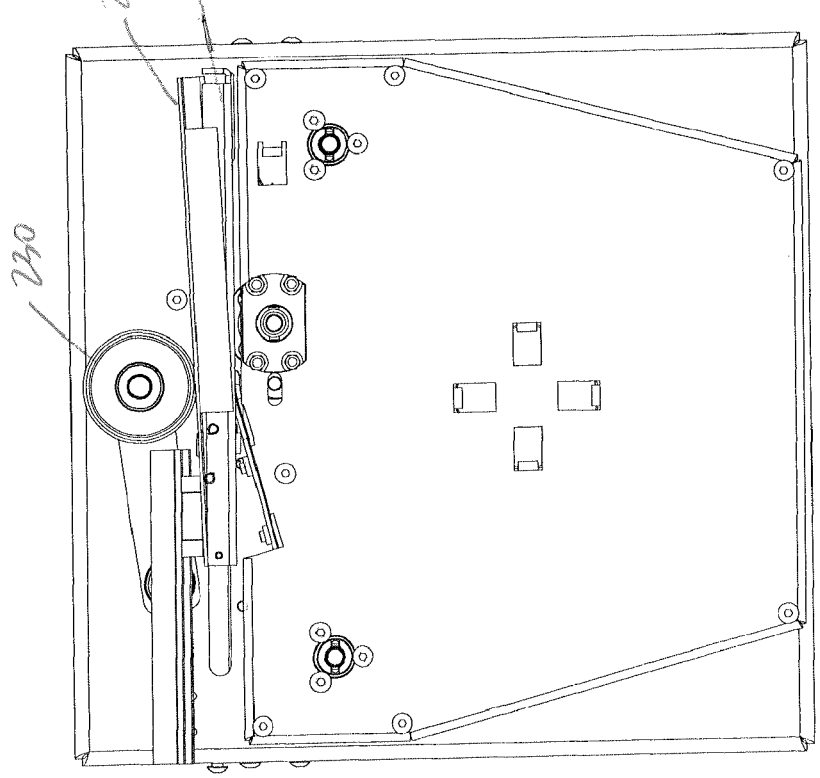
FIG. 14G is a right side view of the laminating device of FIG. 12 with the right sidewall removed to show the elevator in the lowered position.

FIGS. 9-11 depict a device 90 for dispensing a conductive gel according to this aspect of the invention. In particular, the device 90 is a dispenser for providing conductive gels that can be applied to electrodes either manually or in conjunction with a specially designed laminating device. The device 90 has a housing 95, an opening 91 for dispensing the conductive gel, and a hinged door 93 at the top of the housing. Attached to the door 93 is a roller 92 that facilitates the release of the conductive gel. A stack of conductive gels 100 is placed in the housing on a platform 105. Attached to the underside of the platform 105 are springs 101-103. The number of springs can vary depending upon the size of the device 90, the number of conductive gels 100 to be placed in the device, etc. Applying pressure to the stack 100 compresses the springs 101-103. When it is desirable to dispense a conductive gel 100, the roller 92 is rotated to manually dispense the conductive gel. It is also contemplated that the roller 92 can be rotated with the use of a small motor to automatically dispense the gel 100. When the gel 100 is dispensed, it is sandwiched between two protective liners, as described above. One of the protective liners is peeled from the gel 100 and the gel is applied to the electrode. Then the second liner can be removed when the electrode is ready for use. The dispenser as shown in FIGS. 9-11 is lightweight and portable.

FIGS. 12-31 show an electrode laminating device 203 according to a second example embodiment of the present invention. In the first embodiment described above, the laminating device 1 has a roll of conductive gel-pads, a gel-pad delivery mechanism, a gel-pad applicator mechanism, and a drive mechanism all arranged within a single housing. In the second embodiment, the laminating device 203 houses the gel-pad applicator mechanism and the drive mechanism. But the conductive gel-pad roll and the gel-pad delivery mechanism are provided in a replaceable cartridge 208.

The laminating device 203 is used to apply gel-pads 220 to electrodes 232. The gel-pads 220 and the electrodes 232 can be of the same or similar types as those used in conjunction with the laminating device 1 described above.

As shown in FIGS. 12 and 13, the laminating device 1 includes a first housing 212 and the cartridge 208 includes a second housing 210. In the depicted embodiment, the housing 212 of the laminating device 212 includes a main housing portion 212a and an overhanging housing portion 212b (referred to herein collectively as the "housing 212") that are mounted together. In alternative embodiments, the main and overhanging housing portions are integrally formed as one piece.

FIGS. 14a-14h show a carriage assembly 200 of the applicator mechanism. The carriage 200 includes a tray 260 with an electrode opening 201 and an open rear end 207. One of the gel-pads 220 is received through the open rear end 207 and one of the electrodes 232 is received on the tray 260 with the bottom surface of the electrode exposed through the electrode opening 201. The carriage 200 also includes a spring-biased elevator 240 with includes flanges 261 that support the electrode 232 above the surface of the tray 260 a sufficient distance to allow space for the gel-pad 220 (see also FIG. 12). The carriage 200 also includes a blade 202 that is secured to the tray 260 by fasteners, such as bolts 206 inserted through holes 205 in the blade. The blade 202 has a tapered leading edge 204 that is positioned adjacent the gel-pad opening and that overlaps with a leading edge of the gel-pad 220 to provide a pinched zone of the gel-pad (see FIG. 14d). In this way, when the electrode 232 is compressed down onto the gel-pad 220 and the carriage 200 moved from a retracted position (see FIG. 26) toward an extended position (see FIG. 12), this pinched zone will be frictionally held in place to pull the gel-pad (which tends to be extremely sticky from the adhesive) from the protective liner 218 and along with the carriage and electrode. In addition, FIGS. 14e-h show a spring-biased elevator of the carriage 200, details of which are described below.

Figure 17:
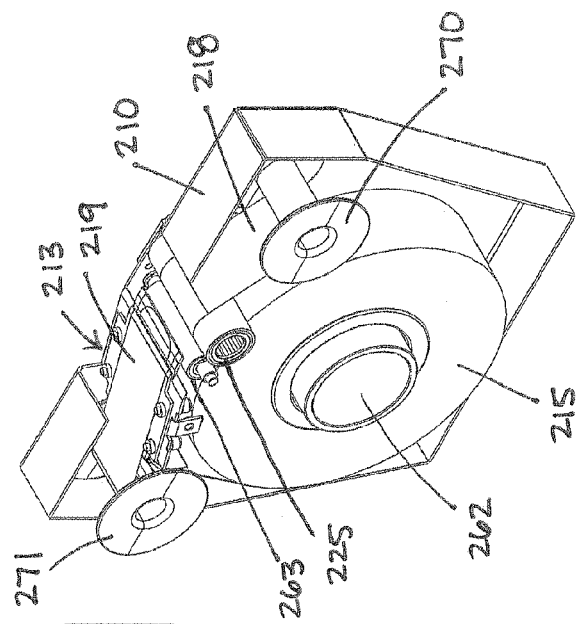
FIG. 17 shows the gel-pad cartridge of FIG. 15 with one of the walls removed to reveal the interior components.
Figure 16:
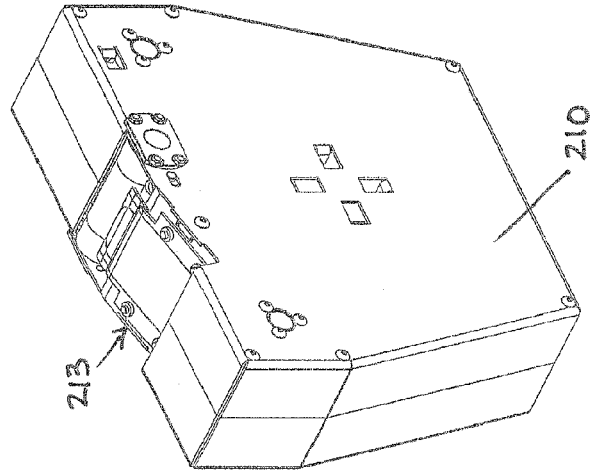
FIG. 16 is a rear/left perspective view of the gel-pad cartridge of FIG. 12.
Figure 15:
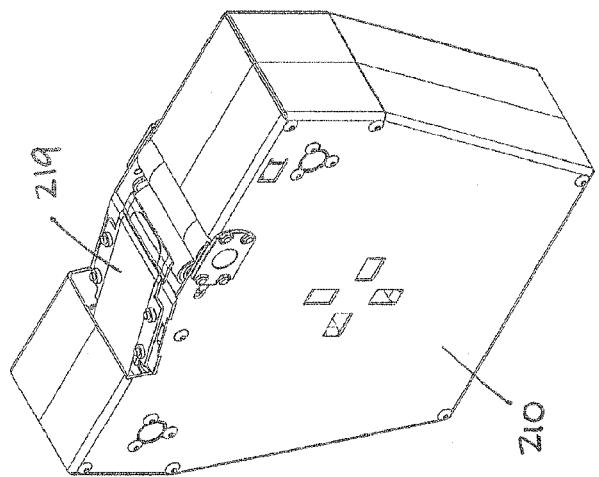
FIG. 15 is a front/left perspective view of the gel-pad cartridge of FIG. 12.

FIGS. 15-17 show details of the major components of the replaceable gel-pad cartridge 208. The gel-pad cartridge 208 includes a roll 215 of the conductive gel-pads 220 mounted onto a spool 262. As mentioned above, in addition to the gel-pad roll 215, the cartridge 208 includes the gel-pad delivery mechanism. In particular, the cartridge 208 includes the two take-up rollers 270 and 271 for reeling in and storing the protective liners 218 and 219 after they have been peeled off of the gel-pads 220. In addition, the cartridge 208 includes the first pressure roller 225 as well as a guide roller 264 and a separator mechanism 213. The first pressure roller 225 pulls on the first protective liner 218 to feed the gel-pad tape (the gel-pads 220 and the protective liners 218 and 219) through the separator mechanism 213, which separates the protective liners from the gel-pads. After separation, the first pressure roller 225 further pulls the first protective liner 218 around the guide roller 264. Then the excess first liner 218 is reeled in by the first take-up roller 270 and the excess second liner 219 is reeled in by the second take-up roller 271.

FIGS. 18a-b and 19 show details of the separator mechanism 213, which is positioned immediately below the carriage 200 when the cartridge 208 is installed on the device 203. The separator mechanism 213 includes a bottom plate 217 and a top plate 215. The two plates 215 and 217 are preferably compressed together with springs, for example, four coil springs 216. In this way, the two plates 215 and 217 apply compressive force to the gel tap between them, thereby acting as a brake and applying a fixed amount of drag to retain the desired amount of tension in the tape as the gel-pads 220 are delivered to the ready position adjacent the electrode 232. In addition, the top and bottom plates 215 and 217 have separating edges 265 and 266, respectively. The second take-up roller 271 pulls the second liner 219 back about 180 degrees around the separating edge 265 of the top plate 215 to remove it from the underlying gel-pad 200. And the guide roller 264 directs the first liner 270 back about 180 degrees around the separating edge 266 of the bottom plate 217 to remove it from the gel-pad 200. (It should be noted that for clarity in FIGS. 18a-b and 19 the gel-tape is not shown being fed into between the top and bottom plates 215 and 217 of the separator mechanism 213.)

FIG. 20 shows the electrode laminating device 203 without the overhanging housing portion 212b and FIG. 21 shows the device 203 without the overhanging housing portion and with the right wall of the housing 212 removed. The carriage 200 is shown having an electrode 232 placed on it. In the depicted embodiment, the gel-pad 220 feeds past the blade 202 of the carriage 200 (see FIGS. 14a-c) by approximately 0.010 inches before being applied to the electrode 232, though this length may be different in other designs. In addition, the applicator mechanism includes a second pressure roller 230 for compressing the conductive gel 220 onto the electrode 232.

In the depicted embodiment, the drive mechanism includes two actuators (e.g., rotary motors) that drive the gel-pad delivery mechanism and the gel-pad applicator mechanism electrode of the laminating device 203. The first motor is the gel transport motor 224 and the second is the carriage motor 226. It will be understood that in other embodiments the drive mechanism can include only one actuator that drives all of the components of the delivery and applicator mechanisms or more than two actuators that drive various of the components of the mechanisms.

The transport motor 224 drives a first pressure roller driver 227 and take-up roller drivers 267 and 268 (e.g., rotary drive shafts). The first pressure roller driver 227, in turn, engages and drives the first pressure roller 225 of the gel-pad cartridge 208 when the cartridge is mounted to the device 203 for use. Similarly, the take-up roller drivers 267 and 268, in turn, engage and drive the take-up rollers 270 and 271, respectively of the gel-pad cartridge 208 when the cartridge is mounted to the device 203 for use. (Actually, in the depicted embodiment the cartridge 208 mounts to the device 203 at least in part by the driver roller 225 and the take-up rollers 270 and 271 of the cartridge engaging and being supported by the respective drivers 227, 267, and 268 of the device.) In the depicted embodiment, the transport motor 224 drives the first pressure roller driver 227 directly and drives the take-up roller drivers 267 and 268 indirectly, for example by driving a linkage 234 (e.g., a belt or chain) operably coupled to the take-up roller drivers and the first pressure roller driver.

The carriage motor 226 controls the position of the second pressure roller 230, for example by driving a cam 242 that drives a follower 269 coupled to an extension arm coupled to the roller. In this way, the cam 242 displaces the second pressure roller 230 from the carriage 200 (e.g., upward in the depicted embodiment) when its pressure and rotation are not needed. In a typical commercial embodiment, for example, two hundred seventy degrees of the rotation of the second pressure roller 230 is used to assist in transporting the carriage 200 from the retracted position to the extended position. When not lowered and ejecting the carriage 200, the second pressure roller 230 is displaced from the carriage 200 and idle.

In addition, the carriage motor 226 controls the position of the carriage 200. In the depicted embodiment, for example, the carriage motor 226 directly drives the cam 242, which in turn drives a linkage 236 (e.g., a belt or chain) that engages and drives the carriage 200 in one direction from the extended to the retracted position. The linkage 236 may one-way drive the carriage 200 for example by a block 237 on the linkage that releasably engages a pin 238 on the carriage (see FIGS. 22 and 24a) or by other mating engagement elements, or they may be operably interrelated by other conventional structures known in the art. The block 237 pushes on the pin 238 to push the carriage 200 into the retracted position. The carriage 200 is held in the retracted position by the block 237 on the belt 236 until a sensor of the control system detects that the gel 220 is driven far enough to just begin riding up on the tapered edge 204 of the blade 202. The gel sensor then signals the control system to turn on the carriage motor 236 to rotate the cam 242 enough to lower the pressure roller 230. Hence the carriage 200 is then free to move.

The use of the laminating device 203 will now be described in conjunction with describing additional components of the device. FIGS. 22 and 23 show the laminating device 203 in an idle (home) position. The elevator 240 begins in an up position (see FIG. 14e-f). The elevator 240 keeps the electrode elevated off of the gel 220 while waiting in the carriage 200. Further, the elevator 240 has springs that bias the elevator upward and but are overcome by downward pressure from the second pressure roller 230 to force the elevator to the down position (see FIGS. 14g-h).

When the pressure roller 230 is moved to the lowered position, the contact between the pressure roller and the electrode 232 overpowers the elevator springs, which otherwise hold the elevator 240 in the raised position. Thus, the elevator 240 lowers and rails along the sides of the elevator engage the first pressure roller 225. With the rails engaged on the first pressure roller 225, the same friction mechanism that moves the gel 220 forward also moves the carriage 220 forward. Consequently, the displacement, velocity, and acceleration are matched between the critical elements and a uniform (bubble- and wrinkle-free) lamination results.

When the device 203 is in the idle position, the second pressure roller 230 is in a displaced position (i.e., raised) positioned away from the carriage 200. When the second pressure roller 230 of the depicted embodiment is lowered, it applies a pressure of approximately 15 pounds to the electrode 232. Also, the carriage 200 is in the extended position awaiting the placement of an electrode 232. In addition, the cam 242 is in a home position, with the follower 269 engaging a first cam surface 273 of the cam. In the depicted embodiment, the cam 242 is rotary, the first cam surface 273 has a two-hundred seventy degree circumference, and the resulting ninety degree gap defines a second cam surface 274. Furthermore, in the home position the conductive gel-pad 220 to be applied is covered by the protective liners 218 and 219.

FIG. 24A shows the carriage 200 in the idle position without an electrode. And FIG. 24B shows the carriage 200 after the operator has inserted an electrode 232 onto it.

Figure 25:
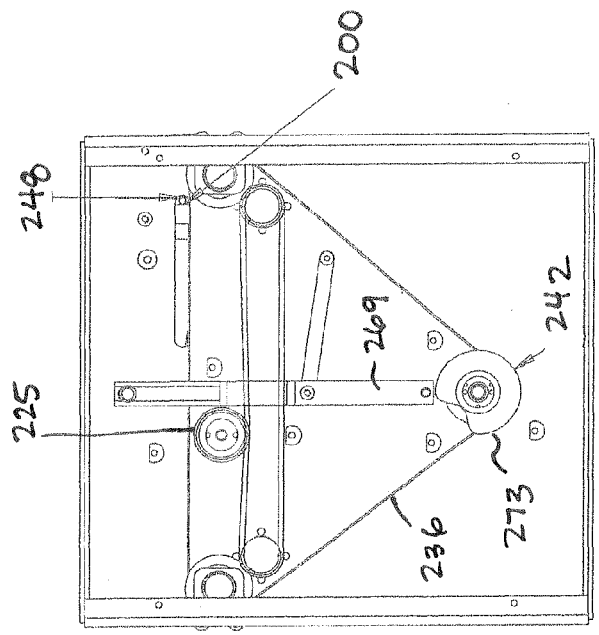
FIG. 25 is a right side view of the laminating device of FIG. 12 with the right sidewall and drive motors removed to show the interior components in an electrode-loaded position.
Figure 26:
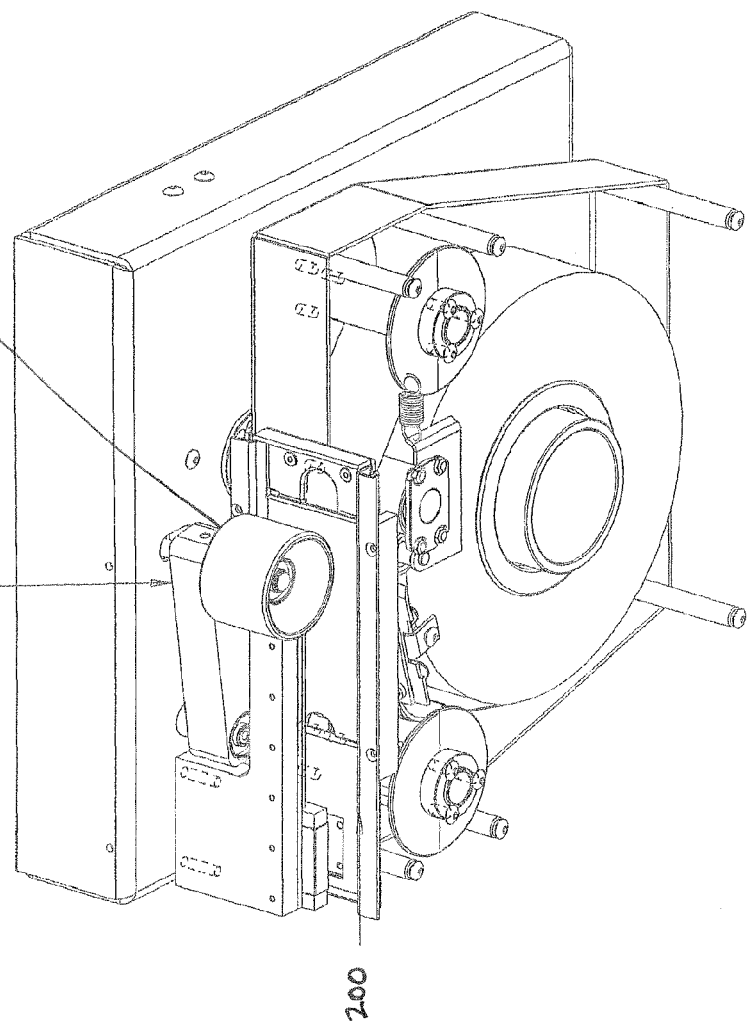
FIG. 26 is a top perspective view of the laminating device of FIG. 12 with the left sidewall and the overhanging housing portion removed to show the interior components in the electrode-loaded position.

After the operator places an electrode 232 into the carriage 200, the operator then activates the device 203 to initiate the laminating process. The laminating device 203 includes a control system having conventional controller components, and the device is activated for example by depressing a "start" button of the control system. As shown in FIGS. 25 and 26, upon activation of the device 203, the control system activates the carriage drive motor 226 to rotate the cam 242 (as indicated by the directional arrow in FIG. 25) so that the follower 269 traverses the first cam surface 273 (e.g., two hundred seventy degrees). The second pressure roller 230 remains elevated at this point. In addition, the rotating cam 242 drives the carriage belt 236, which in turn drives the carriage 200 inwardly to the retracted position within the housing 212b. When the carriage is fully retracted, it engages and activates a limit switch 248 (or a functionally equivalent control device) of the control system that de-activates the second drive motor 226. The laminating device 203 is now in the electrode-loaded position.

Figure 28:
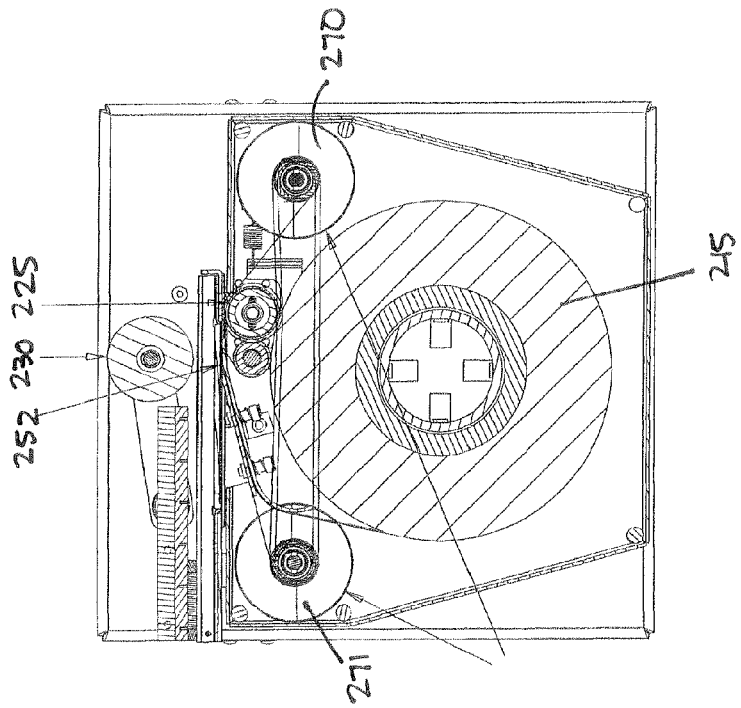
FIG. 28 is an elevational cross section view of the laminating device taken at line 28-28 of FIG. 29 showing the interior components in the ready position.
Figure 29:
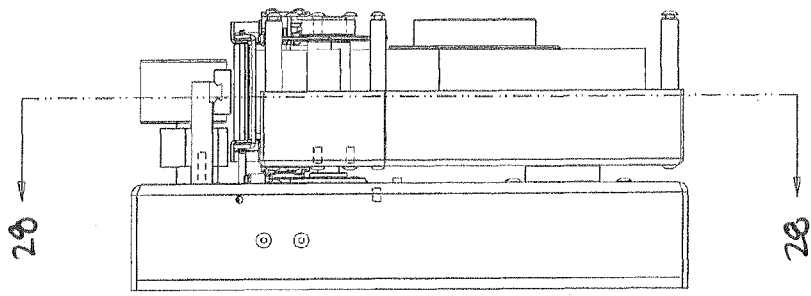
FIG. 29 is a rear view of the laminating device of FIG. 12 with the left side wall of the applicator device removed.
Figure 27:
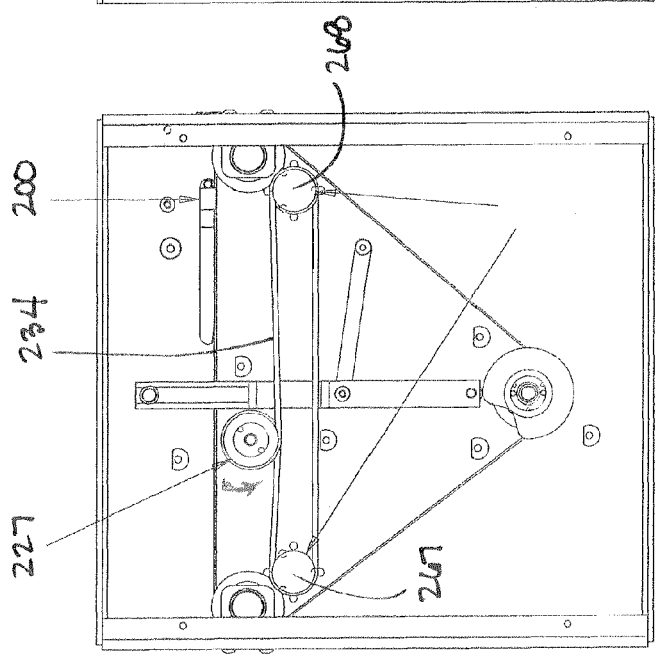
FIG. 27 is a right side view of the laminating device of FIG. 12 with the right sidewall and the drive motors removed to show the interior components in a ready position.

At this point, the control system activates the transport motor 224 to advance the roll of conducting gel 220. As shown in FIGS. 27-29, when the transport motor 224 has rotated the first pressure roller 225 (as indicated by the directional arrow in FIG. 27) to advance one of the gel-pads 220 through the separator mechanism 213 into its ready position adjacent the electrode 232 on the carriage 200, a sensor 252 (or a functionally equivalent control device) of the control system detects contact of the blade 202 in the carriage 200 and by the gel-pad. In addition, the take-up rollers 270 and 271 are rotated by the transport motor 224 to collect the removed protective liners 218 and 219, which are no longer needed. The sensor 252 then sends a signal to the control system, which de-activates the transport motor 224. The carriage 200 is fixed in the retracted position by the cam belt 236 and the second pressure roller 230 remains elevated. The laminating device 203 is now in the ready position.

Figure 30:
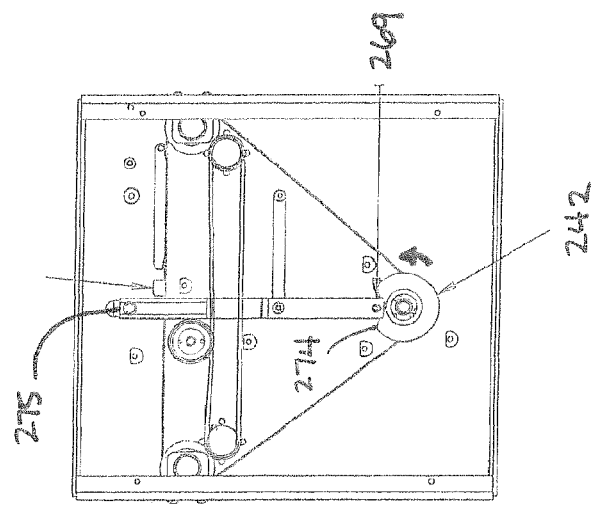
FIG. 30 is a right side view of the laminating device of FIG. 12 with the right sidewall and the drive motors removed to show the internal components in a compressing position.
Figure 32:
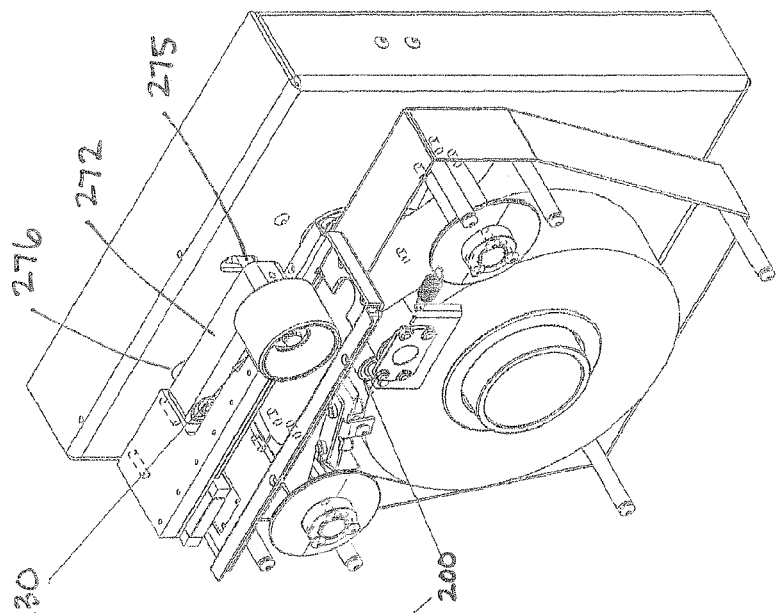
FIG. 32 is a front/left perspective view of the laminating device of FIG. 31.
Figure 31:
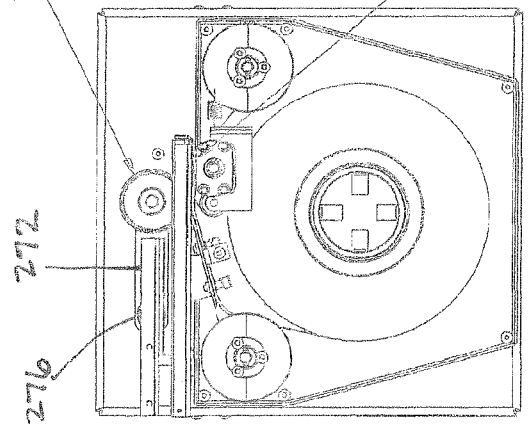
FIG. 31 is a left side view of the laminating device of FIG. 12 with the left sidewall and the overhanging housing portion removed to show the internal components in the compressing position.

With the electrode 232 loaded into the laminating device 203 and the gel-pad 220 delivered to the ready position, the control system then re-activates the carriage motor 226 to compress the gel-pad and the electrode together. FIGS. 30-32 show the laminating device in the compression position. The carriage motor 226 further rotates the cam 242 (as indicated by the directional arrow in FIG. 30) and the cam follower 269 travels across at least a portion of the second cam surface 274. In the depicted embodiment, the second cam surface 274 is defined by a gap in the circumference of the cam 242. As shown, the cam 242 has been further rotated by an additional forty-five degrees, and the cam follower 269 rests at the bottom of the gap of the second cam surface 274. As the follower 269 travels to the bottom of the gap (i.e., the trough) of the second cam surface 274, it moves downward. The follower 269 is coupled to the extension arm 272 by a connecting arm 275 that extends through a slot in the housing. And at one end the extension arm 272 has a pivotal mounting shaft 276 that permits the extension arm to pivot thereabout and at the other end it has the roller 230 mounted to it. In this way, when the follower 269 moves downward, the second pressure roller 230 is pivotally lowered onto the electrode 232. When the second pressure roller 230 lowers to apply pressure, the leading edge of the gel 220 is pinched between the electrode 232 and the separation blade 202 so as to ensure proper separation of the gel from the liner 219 as the carriage 200 is extended. The second pressure roller 230 compresses and the electrode 232 and the leading edge of the conducting gel 220 together on the carriage 200. The laminating device 203 is now in the compressing position. It is further contemplated that a carbon pad can be placed into the carriage 200 along with an electrode 232 and thus compressed by the second pressure roller 242 to also be adhered to the electrode.

As shown in FIGS. 33-35, the control system then re-actives the transport motor 226 to rotate (as indicated by the directional arrow in FIG. 33) the first pressure roller driver 227, which in turn rotates the first pressure roller 225 of the cartridge 208. With the second pressure roller 230 lowered onto the carriage 230, the elevator 240 is now forced down so that the electrode 232 and the gel-pad 220 are compressed together by the second pressure roller (against the bottom plate 217 of the separating mechanism). So the rotation of the first pressure roller 225 imparts a motion to the compressed the electrode 232 and gel-pad 220 assembly, which in turn forces the carriage 200 from the retracted position outward toward the extended position. Simultaneously, the transport motor 224 drives the drivers 267 and 268 for the take-up rollers 207 and 271 to take up the slack in the liners 218 and 219. At this stage, the cam motor 226 remains idle with the follower 269 in the trough of the second cam surface 274. The second pressure roller 230 remains lowered so as to apply pressure to the electrode 232 as the carriage 200 is moved by the first pressure roller 225. In addition, a tension spring 277 may be connected between the take-up roller 271 and the housing (or a frame member connected to the housing) to provide spring-loading between the rollers. Once the carriage 200 is fully extended, the control system deactivates the transport motor 224. The laminating device 203 is now in the done position.

The gel 220 and the electrode 232 are compressed together in the carriage 200 as the carriage is transported to the extended position such that the occurrence of any wrinkles and bubbles is minimized between the gel and electrode. The engagement between the carriage 200 and first pressure roller 225 only occurs when the electrode elevator 240 is pressed down by the second pressure roller 230. Preferably, the laminating device 203 is only operable in a forward direction, so as to maintain tension in the protective liners 218 and 219 transporting the gel.

As shown in FIGS. 36 and 37, the control system then activates the carriage motor 226 to return the laminating device 203 to its home position, and laminated electrode 232 can then be removed from the carriage 200 for use. In particular, cam 242 is reverse-rotated by forty-five degrees to raise the second pressure roller 230, which in turn releases the elevator 240 so that it raises.

In FIG. 38A, the laminated electrode 232 is shown remaining in the carriage 200 with the gel 220 applied to the underside. In FIG. 38B, the electrode 232 is shown inverted with the gel-pad 200 facing upwards and ready for use.

The laminating devices described herein provide numerous advantages over existing devices used to laminate electrodes. The laminating devices are lightweight and portable. The laminating devices described herein can also be handheld devices. The handheld devices can be battery-operated, powered by house voltage from an electrical outlet, or a combination thereof. Alternatively, the devices can be operated manually. The devices described herein are also very easy to maintain (e.g., replace new conductive tape) and use. Thus, the devices described herein are ideal for medical and residential settings where medical electrodes are used. Moreover, the devices do not require expensive heating and cutting mechanisms, thereby ultimately reducing the cost of manufacture and maintenance.

Another advantage of the laminated devices and methods described herein is that the laminated electrodes can be reused without having to dispose of the electrodes after they have been attached to the subject. It is generally undesirable to attach an electrode to a subject if it was previously attached to another subject. The conductive gels laminated on the electrode can be readily peeled off of the electrode after use, and the electrode can be inserted into the laminating device to quickly produce a new laminated electrode. Moreover, the laminating devices described herein are easy to use and do not require the use of alligator clips to secure conductive gels to electrodes, which is cumbersome and labor-intensive.

While the invention has been shown and described in exemplary forms, it will be apparent to those skilled in the art that many modifications, additions, and deletions can be made therein without departing from the spirit and scope of the invention as defined by the following claims.

What is claimed is:

1. A device for laminating to a re-useable medical-use electrode a conductive gel-pad from a series of gel-pads having at least one first protective liner, the device comprising:
   a delivery mechanism including at least one take-up roller that is operable to reel in the liner and deliver the gel-pad to a ready position adjacent the electrode;
   an applicator mechanism including a carriage and a pressure roller, wherein the carriage supports the electrode and the pressure roller applies a compressive force to the electrode to laminate the gel-pad thereto, wherein the carriage moves between an extended position and a retracted position, wherein in the extended position the electrode can be loaded thereonto and in the retracted position the electrode is in the ready position within the laminating device; and
   a drive mechanism including at least one actuator operably coupled to the delivery mechanism and the applicator mechanism to drive the take-up roller and the pressure roller.

2. The laminating device of claim 1, wherein the drive mechanism includes a carriage-driving linkage with an engagement element and the carriage includes an engagement element that mates with and is driven in one direction by the carriage engagement element to move the carriage from an extended position to a retracted position.

3. A device for laminating to a re-useable medical-use electrode a conductive gel-pad from a series of gel-pads having at least one protective liner, the device comprising:
   a delivery mechanism including at least one take-up roller that is operable to reel in the liner and deliver the gel-pad to a ready position adjacent the electrode;
   an applicator mechanism including a carriage and a pressure roller, wherein the carriage supports the electrode and the pressure roller applies a compressive force to the electrode to laminate the gel-pad thereto, wherein the carriage has a gel-pad opening through which a portion of the electrode is exposed and through which the gel-pad extends in the ready position; and
   a drive mechanism including at least one actuator operably coupled to the delivery mechanism and the applicator mechanism to drive the take-up roller and the pressure roller.

4. The laminating device of claim 3, wherein the gel-pad has a leading edge, the carriage includes a blade with a tapered edge positioned adjacent the gel-pad opening, and the leading edge of the gel-pad in the ready position extends through the gel-pad opening and is pinched between the tapered edge of the blade and the electrode on the carriage due to the pressure roller applying a compressive force on the electrode so that the pinched gel-pad is carried with the carriage when the carriage is moved to an extended position, wherein the gel-pad and the electrode are compressed together between the carriage and the pressure roller as the carriage moves to the extended position.

5. The laminating device of claim 1, wherein the delivery mechanism includes a separator mechanism having at least one plate with a separating edge positioned so that the drive mechanism drives the at least one take-up roller to pull the liner across the plate and back around the separating edge to peel the liner from the gel-pad while delivering the gel-pad to the ready position adjacent the electrode.

6. The laminating device of claim 1, wherein the delivery mechanism includes a separator mechanism having two plates that are spring-biased together in compression to apply a braking force to the gel-pads routed between the plates.

7. A device for laminating to a re-useable medical-use electrode a conductive gel-pad from a series of gel-pads having at least one protective liner, the device comprising:
   a delivery mechanism including at least one take-up roller that is operable to reel in the liner and deliver the gel-pad to a ready position adjacent the electrode;
   an applicator mechanism including a carriage and a pressure roller, wherein the carriage supports the electrode and the pressure roller applies a compressive force to the electrode to laminate the gel-pad thereto, wherein the carriage includes a tray and an elevator, wherein the tray has an opening through which a portion of the electrode is exposed and through which the gel-pad extends in the ready position, and wherein the elevator supports the electrode and is spring-biased away from the tray toward an elevated position in which the electrode is displaced away from the gel-pad in the ready position; and
   a drive mechanism including at least one actuator operably coupled to the delivery mechanism and the applicator mechanism to drive the take-up roller and the pressure roller.

8. The laminating device of claim 7, wherein the pressure roller moves from a displaced position away from the carriage to a compressing position, wherein in the compressing position the pressure roller compresses against the electrode in the elevator to depress the electrode and the elevator to a compressing position to adhere the gel pad to the electrode together.

9. The laminating device of claim 8, wherein the drive mechanism includes a cam and a cam follower, the cam follower is coupled to the pressure roller, and the pressure roller is moved from the displaced position to the compressing position by the drive mechanism driving the cam.

10. A device for laminating to a re-useable medical-use electrode a conductive gel-pad from a series of gel-pads having at least one protective liner, the device comprising:
   a delivery mechanism including at least one take-up roller that is operable to reel in the liner and deliver the gel-pad to a ready position adjacent the electrode;
   an applicator mechanism including a carriage and a pressure roller, wherein the carriage supports the electrode and the pressure roller applies a compressive force to the electrode to laminate the gel-pad thereto; and
   a drive mechanism including at least one actuator operably coupled to the delivery mechanism and the applicator mechanism to drive the take-up roller and the pressure roller, wherein the delivery mechanism includes a second pressure roller that cooperates with the applicator pressure roller to impart motion to the carriage to move the carriage from a retracted position to an extended position, wherein the pressure rollers further cooperate to compress the gel-pad onto the electrode as the carriage is moved to the extended position.

11. A device for use with a replaceable gel-pad cartridge to laminate a re-useable medical-use electrode, the cartridge including a series of gel-pads, a liner covering the gel-pads, and a delivery mechanism including at least one take-up roller that is operable to reel in the liner and sequentially deliver the gel-pads to a ready position adjacent the electrode, the device comprising:
   an applicator mechanism including a carriage and a pressure roller, wherein the carriage supports the electrode and the pressure roller applies a compressive force to the electrode to laminate the gel-pad in the ready position thereto, wherein the carriage moves between an extended position and a retracted position, wherein in the extended position the electrode can be loaded thereonto and in the retracted position the electrode is in the ready position within the laminating device; and
   a drive mechanism including at least one actuator operably coupled to the delivery mechanism and the applicator mechanism to drive the take-up roller and the pressure roller.

12. The laminating device of claim 11, wherein the drive mechanism includes a carriage-driving linkage with an engagement element and the carriage includes an engagement element that mates with and is driven in one direction by the carriage engagement element to move the carriage from an extended position to a retracted position.

13. A device for use with a replaceable gel-pad cartridge to laminate a re-useable medical-use electrode, the cartridge including a series of gel-pads, a liner covering the gel-pads, and a delivery mechanism including at least one take-up roller that is operable to reel in the liner and sequentially deliver the gel-pads to a ready position adjacent the electrode, the device comprising:
   an applicator mechanism including a carriage and a pressure roller, wherein the carriage supports the electrode and the pressure roller applies a compressive force to the electrode to laminate the gel-pad in the ready position thereto, wherein the carriage has a gel-pad opening through which a portion of the electrode is exposed and through which the gel-pad extends in the ready position; and
   a drive mechanism including at least one actuator operably coupled to the delivery mechanism and the applicator mechanism to drive the take-up roller and the pressure roller.

14. The laminating device of claim 13, wherein the ready-positioned gel-pad has a leading edge, the carriage includes a blade with a tapered edge positioned adjacent the gel-pad opening, and the leading edge of the gel-pad in the ready position extends through the gel-pad opening and is pinched between the tapered edge of the blade and the electrode on the carriage due to the pressure roller applying a compressive force on the electrode so that the pinched gel-pad is carried with the electrode and the carriage when the carriage is moved to an extended position, wherein the gel-pad and the electrode are compressed together between the carriage and the pressure roller as the carriage moves to the extended position.

15. The laminating device of claim 11, wherein the carriage includes a tray and an elevator, wherein the tray has an opening through which a portion of the electrode is exposed and through which the gel-pad extends in the ready position, and wherein the elevator supports the electrode and is spring-biased away from the tray toward an elevated position in which the electrode is displaced away from the gel-pad in the ready position.

16. The laminating device of claim 15, wherein the pressure roller moves from a displaced position away from the carriage to a compressing position, wherein in the compressing position the pressure roller compresses against the electrode in the elevator to depress the electrode and the elevator to a compressing position to adhere the gel pad to the electrode together.

17. The laminating device of claim 16, wherein the drive mechanism includes a cam and a cam follower, the cam follower is coupled to the pressure roller, and the pressure roller is moved from the displaced position to the compressing position by the drive mechanism driving the cam.

18. The laminating device of claim 11, wherein the drive mechanism includes a driver that engages and drives the take-up roller and a driver that engages and drives the pressure roller.

19. The laminating device of claim 1, wherein the gel-pad includes a second protective liner and is interposed between the first and second liners.

20. The laminating device of claim 5, wherein the separating edge of the separator plate is a tapered leading edge that overlaps with a leading edge of the gel-pad to pinch the gel-pad against the electrode in the ready position.

* * * * *